(12) United States Patent
Podesta et al.

(10) Patent No.: US 9,737,515 B2
(45) Date of Patent: Aug. 22, 2017

(54) COMPOSITIONS AND METHODS FOR INHIBITING TUMOR GROWTH

(71) Applicants: Ernesto Jorge Podesta, Ciudad Autonoma de Buenos Aires (AR); Paula Mariana Maloberti, Ciudad Autonoma de Buenos Aires (AR); Ulises Daniel Orlando, Pcia. de Buenos Aires (AR); Melina Andrea Dattilo, Pcia. de Buenos Aires (AR); Ana Fernanda Castillo, Ciudad Autonoma de Buenos Aires (AR); Angela Rosaria Solano, Ciudad Autonoma de Buenos Aires (AR)

(72) Inventors: Ernesto Jorge Podesta, Ciudad Autonoma de Buenos Aires (AR); Paula Mariana Maloberti, Ciudad Autonoma de Buenos Aires (AR); Ulises Daniel Orlando, Pcia. de Buenos Aires (AR); Melina Andrea Dattilo, Pcia. de Buenos Aires (AR); Ana Fernanda Castillo, Ciudad Autonoma de Buenos Aires (AR); Angela Rosaria Solano, Ciudad Autonoma de Buenos Aires (AR)

(73) Assignee: Consejo Nacional De Investigaciones Cientificas Y Tecnicas (CONICET), Buenos Aires (AR)

( * ) Notice: Subject to any disclaimer, the term of this patent is extended or adjusted under 35 U.S.C. 154(b) by 0 days.

(21) Appl. No.: 15/058,916

(22) Filed: Mar. 2, 2016

(65) Prior Publication Data
US 2016/0303090 A1 Oct. 20, 2016

Related U.S. Application Data

(60) Provisional application No. 62/127,465, filed on Mar. 3, 2015.

(51) Int. Cl.
| | | |
|---|---|---|
| A61K 31/138 | (2006.01) |
| A61K 31/436 | (2006.01) |
| A61K 31/4439 | (2006.01) |
| A61K 45/06 | (2006.01) |

(52) U.S. Cl.
CPC .......... *A61K 31/436* (2013.01); *A61K 31/138* (2013.01); *A61K 31/4439* (2013.01); *A61K 45/06* (2013.01)

(58) Field of Classification Search
CPC . A61K 31/436; A61K 31/4439; A61K 31/138
See application file for complete search history.

(56) References Cited

U.S. PATENT DOCUMENTS

2006/0264384 A1* 11/2006 Johansen ............. A61K 31/366
514/27

OTHER PUBLICATIONS

Mody et al. Endocrine Related Cancer, 2007, vol. 14, pp. 305-315.*
Zhong et al. Zhongguo Zhongliu Linchuang, 2010, vol. 37, No. 11, see abstract.*
Gelmon et al., "Targeting triple-negative breast cancer: optimising therapeutic outcomes," Ann Oncol, 23, 2012, pp. 2223-2234.
Ghayad et al., "mTOR inhibition reverses acquired endocrine therapy resistance of breast cancer cells at the cell proliferation and gene-expression levels," Cancer Sci., 2008; 99(10), pp. 1992-2003.
Kang et al., "A novel arachidonate-preferring acyl-CoA synthetase is present in steroidogenic cells of the rat adrenal, ovary, and testis," Proc Natl Aced Sci USA, 94, 1997, pp. 2880-2884.
Luconi et al., "Rosiglitazone impairs proliferation of human adrenocortical cancer: preclinical study in a xenograft mouse model," Endocr Relat Cancer, 17, 2010, pp. 169-177.
Maloberti et al., "Silencing the expression of mitochondrial acyl-CoA thioesterase I and acyl-CoA synthetase 4 inhibits hormone-induced steroidogenesis," Febs J, 272, 2005, pp. 1804-1814.
Maloberti et al., "Functional interaction between acyl-CoA synthetase 4, lipooxygenases and cyclooxygenase-2 in the aggressive phenotype of breast cancer cells," PLoS One, 5, 2010, pp. e15540.
Modi et al., "Propylisopropylacetic acid (PIA), a constitutional isomer of valproic acid, uncompetitively inhibits arachidonic acid acylation by rat acyl-CoA synthetase 4: a potential drug for bipolar disorder," Biochim Biophys Acta, 1831, 2013, pp. 880-886.
Noh et al., "Determinants of rapamycin sensitivity in breast cancer cells," Clin Cancer Res, 10, 2004, pp. 1013-1023.
Orlando et al., "The functional interaction between Acyl-CoA synthetase 4, 5-lipooxygenase and cyclooxygenase-2 controls tumor growth: a novel therapeutic target," PLoS One, 7, 2012, pp. e40794.
Yardley, "Combining mTOR Inhibitors with Chemotherapy and Other Targeted Therapies in Advanced Breast Cancer: Rationale, Clinical Experience, and Future Directions," Breast Cancer (Auckl), 7, 2013, pp. 7-22.
Vezina et al., "Rapamycin (AY-22,989), a new antifungal antibiotic. I. Taxonomy of the producing streptomycete and isolation of the active principle," J Antibiot (Tokyo), 28(10), Oct. 1975, pp. 721-726.
Orlando et al., "Acyl-CoA synthetase-4, a new regulator of mTOR and a potential; therapeutic target for enhanced estrogen receptor function in receptor-positive and -negative breast cancer," Oncotarget, vol. 6, No. 40, Oct. 19, 2015, pp. 43632-43650.
Castillo et al., "Acyl-Coa synthetase-4, a new potential therapeutic target in hormone-resistant breast cancer," Biocell, 39 (Suppl. 2), Nov. 2015, Abstract, pp. 1.

(Continued)

*Primary Examiner* — Samira Jean-Louis
(74) *Attorney, Agent, or Firm* — Muncy, Geissler, Olds & Lowe, P.C.

(57) ABSTRACT

The present invention relates to compositions and methods for preventing and treating cell proliferation in cancer. More specifically, the present invention relates to compositions and methods for inhibiting tumor growth, and for treating proliferative diseases, particularly colon and breast cancer, with a combined pharmacological approach. Yet more specifically, the compositions for inhibiting tumor growth comprise a combination of: i) a first component which is an ACSL4 inhibitor; and ii) a second component selected from the group consisting of mTOR inhibitor and ER inhibitor.

7 Claims, 8 Drawing Sheets

(56) References Cited

OTHER PUBLICATIONS

Orlando et al., "Vías de señalización reguladas por Acil-Coa-sinetasa-4: posibles nuevos blancos terapéuticos combinados trabajando en forma sinérgica para el tratamiento de tumores de mama triple negativos y refractarios al tratamiento hormonal," Revista Medicina, vol. 75, Supl II-2015, Nov. 2015, Abstract (104), pp. 82-83.

* cited by examiner

COMPOSITIONS AND METHODS FOR INHIBITING TUMOR GROWTH

FIELD OF THE INVENTION

The present invention relates to compositions and methods for preventing and treating proliferative diseases, such as cancer. More specifically, the present invention relates to compositions and methods for inhibiting tumor growth, particularly breast and colon cancer, in a combined pharmacological treatment. In a preferred embodiment, the invention provides a synergistic pharmaceutical composition for inhibiting tumor growth comprising a combination of: i) a first component which is an ACSL4 inhibitor; and ii) a second component selected from the group consisting of mTOR inhibitor and ER inhibitor.

BACKGROUND OF THE INVENTION

Breast cancer comprises a heterogeneous group of diseases that vary in morphology, biology, behavior and response to therapy. Among women, breast cancer remains the second most important cause of death (by cancer). Patients who cannot be cured are those in whom breast cancer has metastasized, that is, breast cancer cells have migrated and invaded other organs such as lung and bone.

Triple-negative breast cancer (estrogen-receptor-$\alpha$ (ER)-negative, progesterone-receptor (PR)-negative, and human epidermal growth factor 2 receptor (HER2)-non overexpressed) is a subtype of breast cancer that accounts for approximately 15% of breast cancer. Triple-negative breast cancer (TNBC) is a subtype of tumor known for its aggressive clinical behavior.

Triple negative breast cancer and endocrine-resistant breast cancer tumors are an important area of research for both researchers and clinicians alike for being poor prognostic factors for disease-free and overall survival. Besides, no effective specific targeted therapy is readily available therefor.

Previous studies have identified an acyl-CoA synthetase 4 (ACSL4) gene-expression pattern correlated with triple-negative tumors. It has been shown that both in breast cancer cell lines and in tumor samples the expression of acyl-CoA synthetase 4 (ACSL4) is inversely correlated with ER levels. ACSL4 belongs to a five-member family of enzymes that esterifies mainly arachidonic acid (AA) into acyl-CoA (Maloberti P. M. et al., 2010; Functional interaction between acyl-CoA synthetase 4, lipooxygenases and cyclooxygenase-2 in the aggressive phenotype of breast cancer cells. PLoS One 5, e15540; Orlando, U. D. et al., 2012; The functional interaction between Acyl-CoA synthetase 4, 5-lipooxygenase and cyclooxygenase-2 controls tumor growth: a novel therapeutic target. PLoS One 7, e40794.) and, unlike the other ACSL isoforms, ACSL4 is encoded on the X chromosome and its expression is highest in adrenal cortex, ovary and testis (Kang, M. J. et al., 1997; A novel arachidonate-preferring acyl-CoA synthetase is present in steroidogenic cells of the rat adrenal, ovary, and testis. Proc Natl Acad Sci USA 94, 2880-2884.). ACSL4 is also highly expressed in mouse and human cerebellum and hippocampus. The physiological functions of ACSL4 have been studied and include possible roles in polyunsaturated fatty acid metabolism in brain, in steroidogenesis and in eicosanoid metabolism related to apoptosis (Maloberti P. M. et al., 2005; Silencing the expression of mitochondrial acyl-CoA thioesterase I and acyl-CoA synthetase 4 inhibits hormone-induced steroidogenesis. Febs J 272, 1804-1814.). ACSL4 expression has also been associated with non-physiological functions such as mental retardation disorder (Modi, H. R. et al., 2013; Propylisopropylacetic acid (PIA), a constitutional isomer of valproic acid, uncompetitively inhibits arachidonic acid acylation by rat acyl-CoA synthetase 4: a potential drug for bipolar disorder. Biochim Biophys Acta 1831, 880-886.) and cancer (Maloberti P. M. et al., 2010, supra). ACSL4 was first associated with cancer due to its abnormal expression in colon and hepatocellular carcinoma. Increased ACSL4 expression, both at mRNA and protein levels, in colon adenocarcinoma cells has been associated with the inhibition of apoptosis and an increase in cell proliferation when compared to adjacent normal tissue. ACSL4 has also been suggested as a predictive factor for drug resistance in breast cancer patients receiving adriamycin-containing chemotherapy.

The present inventors have demonstrated a positive correlation of ACSL4 expression and aggressiveness in breast cancer cell lines, with the highest expression found in metastatic lines derived from triple-negative tumor breast cancer (MDA-MB-231 and Hs578T) (Maloberti P. M. et al., 2010, supra). Functionally, it was found that ACSL4 is part of the mechanism responsible for increased breast cancer cell proliferation, invasion and migration, both in vitro and in vivo (Maloberti P. M. et al., supra, 2010; Orlando U. D. et al., 2012, supra). Accordingly, the sole transfection of MCF-7 cells, a model of non-aggressive breast cancer cells, with ACSL4 cDNA transforms them into a highly aggressive phenotype, and it was further demonstrated that ACSL4 can be silenced to reduce cell line aggressiveness. Furthermore, the stable transfection of MCF-7 cells with ACSL4 using the tetracycline Tet-Off system (MCF-7 Tet-Off/ACSL4) and their injection into nude mice has resulted in the development of growing tumors with marked nuclear polymorphism, a high mitotic index and low expression of ER and PR (Orlando U. D. et al., 2012 supra), all of which demonstrates the transformational capacity of ACSL4 overexpression. The role of ACSL4 in the development of growing tumors found further support when tumor growth was inhibited through the inhibition of ACSL4 expression by treating mice with doxycycline. Although the role of ACSL4 in mediating the aggressive phenotype in breast cancer is well accepted, the mechanism involved in this effect has yet to be fully elucidated. And, as enzyme overexpression can solely change cell phenotype from mildly aggressive to highly aggressive, the MCF-7 Tet-Off/ACSL4 model may be regarded as a valuable technique to study the mechanisms through which ACSL4 triggers the phenotype change.

The idea of personalized medicine and molecular profiling for prognostic tests has led to a plethora of studies in the past 10 years, in search for genetic determinants of metastatic breast cancer. Such studies have identified gene sets, or "signatures", whose expression in primary tumors is associated with higher risk of metastasis and poor disease outcome for the patients.

The present application discloses experimental evidence of the role played by the ACSL4 overexpression in the aggressive phenotype of TNBC.

Although the role of ACSL4 in mediating an aggressive phenotype in breast cancer is well accepted, there is little evidence as to the early steps through which ACSL4 increases tumor growth and progression. Therefore, the present inventors performed a massive in-depth mRNA sequencing approach and the reverse-phase protein array using MCF-7 Tet-Off/ACSL4 as a model to identify gene expression and functional proteomic signatures specific to ACSL4 overexpression. In particular, the present inventors make use of the tetracycline Tet-Off system to stably transfect non-aggressive breast cancer MCF-7 cells and develop a stable line overexpressing ACSL4 (MCF-7 Tet-Off/ACSL4). As a result, the present inventors have proven that cell transfection solely with ACSL4 cDNA renders a highly aggressive phenotype in vitro and results in lower ER expression and the development of growing tumors when injected into nude mice.

The sole expression of ACSL4 displays a distinctive transcriptome and functional proteomic profile, and results show that the most significantly up-regulated gene networks in breast cancer cells overexpressing ACSL4 include genes associated with the regulation of embryonic and tissue development, cellular movement and DNA replication and repair.

In addition, the present inventors have shown in previous studies that the effects of Rosiglitazone on cell and tumor growth in vitro or in vivo are similar to those obtained with the specific inhibition of ACSL4 by doxycycline treatment of the MCF-7 Tet-Off/ACSL4 (Orlando U. D. et al., 2012, supra), the minimal doses exerting significant inhibitory effects being 75 µM for rosiglitazone.

Rosiglitazone, a member of the thiazolidinedione family of drugs (TZDs), is known to attenuate cell growth in carcinoma of various organs including breast, prostate, lung, colon, stomach, bladder and pancreas. Rosiglitazone and derivatives of troglitazone have been used either alone or in combination in experimental conditions to inhibit the growth of different tumor cell lines (Luconi, M. et al., 2010; Rosiglitazone impairs proliferation of human adrenocortical cancer: preclinical study in a xenograft mouse model. Endocr Relat Cancer 17, 169-177.) and, although the action of rosiglitazone has been attributed to its effects on the peroxisome proliferator-activated receptor gamma, in vitro studies performed with rat recombinant proteins have demonstrated that TZDs can directly inhibit the activity of one of the gene products of the acyl-CoA synthetases, i.e. ACSL4.

Rosiglitazone is an antidiabetic drug in the thiazolidinedione class of drugs. It works as an insulin sensitizer, by binding to the PPAR receptors in fat cells and making the cells more responsive to insulin. Despite rosiglitazone's effectiveness at decreasing blood sugar in type 2 diabetes mellitus, at daily oral dose in the range of 4 to 8 mg, its use decreased dramatically as studies showed apparent associations with increased risks of heart attacks and death. On Sep. 23, 2010 the US Food and Drug Administration issued a decision to restrict access to rosiglitazone medicines. In Europe, the European Medicines Agency (EMA) recommended in September 2010 that the drug be suspended from the European market because the benefits of rosiglitazone no longer outweighed the risks.

Another member of the drug class of thiazolidinediones, Troglitazone, a peroxisome proliferator-activated receptor gamma agonist, which enhances insulin sensitivity, was approved for the treatment of type 2 diabetes in 1997. Troglitazone was available in 400 mg tablets. The recommended dosage was 400 to 800 mg once daily. However, within a year after its widespread use, individual cases of liver injury and failure were reported, leading to the withdrawal of troglitazone from the market in the year 2000.

According to the findings of the present inventors, an ACSL4 overexpression gene and functional proteomic signature was derived which might reveal important information about novel mediators of breast cancer cell aggressiveness. By means of a model of ACSL4 overexpression and a pharmacological approach, it was also showed that ACSL4 and the mTOR pathway from the transcriptome and functional proteomic profile are functionally required and work in a synergistic way for cell proliferation in the MCF-7 Tet-Off/ACSL4 model.

It is also demonstrated herein that ER expression is down-regulated and that specific pathways such as AKT-mTOR-SP6 kinase and Wnt (Wingless-Type MMTV Integration Site Family) are functionally required for ACSL4 action.

Rapamycin, also known as sirolimus, is an mTOR inhibitor macrolide, originally identified in sirolimus-resistant mutants of *Saccharomyces* (Vézina C. et al., 1975; Rapamycin (AY-22,989), a new antifungal antibiotic. I. Taxonomy of the producing streptomycete and isolation of the active principle. J Antibiot (Tokyo). 1975 October; 28(10):721-6.). Though it was first developed as an antifungal agent, its immunosuppressive and antiproliferative properties later redirected its use towards the treatment of certain tumors.

Rapamycin and its analogues are being used in clinical trials as novel-targeted anticancer agents and although their activity in this context has been proven, results show that only some of the treated patients actually respond to treatment (Noh W. C. et al., 2004; Determinants of rapamycin sensitivity in breast cancer cells. Clin Cancer Res 10, 1013-1023).

In conclusion, ACSL4 is an upstream regulator of tumorigenic pathways and the data herein provide novel insights into a combined pharmacological approach. Because an aggressive tumor phenotype appears in the early stages of metastatic progression, the previously unknown mediators of ACSL4 might become valuable prognostic tools or therapeutic targets in breast cancer.

SUMMARY OF THE INVENTION

It is an object of the present invention to provide a pharmacological combination which inhibits tumor growth, comprising: i) a first component which is an ACSL4 inhibitor; and ii) a second component selected from the group consisting of mTOR inhibitor and ER inhibitor, wherein the first component is present in therapeutically sub-maximal amounts.

Preferably, the present invention provides a composition for inhibiting tumor growth comprising a combination of: i) a first component which is an ACSL4 inhibitor; and ii) a second component selected from the group of mTOR inhibitor and ER inhibitor.

In a preferred embodiment, the present invention provides a composition for inhibiting tumor growth comprising a synergic combination of: i) a first component which is an ACSL4 inhibitor; and ii) a second component which is an mTOR inhibitor. More specifically, the invention provides a composition for inhibiting tumor growth comprising a synergic combination of rosiglitazone and rapamycin.

In a preferred embodiment, the present invention provides a composition for inhibiting tumor growth comprising a synergic combination of: i) a first component which is an ACSL4 inhibitor; and ii) a second component which is an ER inhibitor. More specifically, the invention provides a composition for inhibiting tumor growth comprising a synergic combination of rosiglitazone and tamoxifen.

According to the invention, the ACSL4 inhibitor is preferably a thiazolidinedione compound, preferably selected from the group of rosiglitazone, pioglitazone and troglitazone, being rosiglitazone the most preferred.

According to the invention, the mTOR inhibitor is selected from rapamycin, temsirolimus, everolimus, tacrolimus, deforolimus, pimecrolimus, olcorolimus, zotarolimus, umirolimus. Preferably, the mTOR inhibitor is rapamycin.

According to the invention, the ER inhibitor is selected from tamoxifen, bazedoxifene, lasofoxifene, ormeloxifene, raloxifene, clomifene, tamoxifen derivatives and analogs (such as 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen, 4-hydroxy-N-demethyl-tamoxifen). Preferably, the ER inhibitor is tamoxifen.

According to a more preferred embodiment, the composition of the invention comprises rosiglitazone and rapamycin.

According to another preferred embodiment of the invention, the composition comprises rosiglitazone and tamoxifen.

Preferably, rosiglitazone is present in the composition of the invention in an amount ranging from 2 to 8 mg/70 kg (body weight).

According to present invention, rapamycin is present in the composition in an amount ranging from 500 μg to 10 mg/60 kg/day. Preferably, the amount of rapamycin is 8 mg/60 kg/day.

According to present invention tamoxifen is present in the composition in an amount ranging from 2 mg to 50 mg/60 kg/day. Preferably, the amount of tamoxifen is 10 mg/60 kg daily.

According to another embodiment, the present invention provides a method for inhibiting tumor growth which comprises administering to a subject in need thereof a combination of: i) a first component which is an ACSL4 inhibitor; and ii) a second component selected from the group of mTOR inhibitor and ER inhibitor.

According to the method of the invention, the tumor is selected from the group consisting of colon carcinoma, hepatocellular carcinoma, prostate cancer, breast cancer, TNBC, as well as other cancers characterized by the overexpression of ACSL4.

According to the method of the invention, the first component is an ACSL4 inhibitor, which is preferably a thiazolidinedione compound, preferably selected from the group of rosiglitazone, pioglitazone and troglitazone, being rosiglitazone the most preferred.

According to the method of the invention, the second component may be a mTOR inhibitor selected from rapamycin, temsirolimus, everolimus, tacrolimus, deforolimus, pimecrolimus, olcorolimus, zotarolimus, umirolimus. Preferably, the mTOR inhibitor is rapamycin.

According to the method of the invention, the second component may be a ER inhibitor which is selected from tamoxifen, bazedoxifene, lasofoxifene, ormeloxifene, raloxifene, clomifene, tamoxifen derivatives and analogs (such as 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen, 4-hydroxy-N-demethyl-tamoxifen). Preferably, the ER inhibitor is tamoxifen.

According to a preferred embodiment, the present invention provides a method for inhibiting tumor growth which comprises administering to a subject in need thereof a synergistic combination of rosiglitazone and rapamycin.

According to a preferred embodiment, the present invention provides a method for inhibiting tumor growth which comprises administering to a subject in need thereof a synergistic combination of rosiglitazone and tamoxifen.

Another object of the present invention is to provide a method for inhibiting tumor growth, wherein the tumor is selected from the group consisting of colon carcinoma, hepatocellular carcinoma, prostate cancer, breast cancer, triple negative breast cancer (TNBC), and other cancers characterized by the overexpression of ACSL4.

These results suggest that ACSL4 could be a target to restore tumor hormone dependence in tumors with poor prognosis for disease-free and overall survival, in which no effective specifically targeted therapy is readily available.

BRIEF DESCRIPTION OF THE DRAWINGS

The following figures form part of the present specification and are included to further demonstrate certain aspects of the present invention.

Data are presented as means±SD. a, b, c, and d: * p<0.001 vs. corresponding single inhibitors; e: * p<0.001 vs. 4-OHTAM 2.5 μM+rosiglitazone 10 μM. (B) MCF-7 Tet-Off/ACSL4 cells were incubated in the presence or absence of rosiglitazone (75 μM) alone or in combination with GW9662 (10 μM) for 24 h. ERα and mTOR-related protein levels were evaluated by Western blot and a representative blot is shown.

Figure 7:
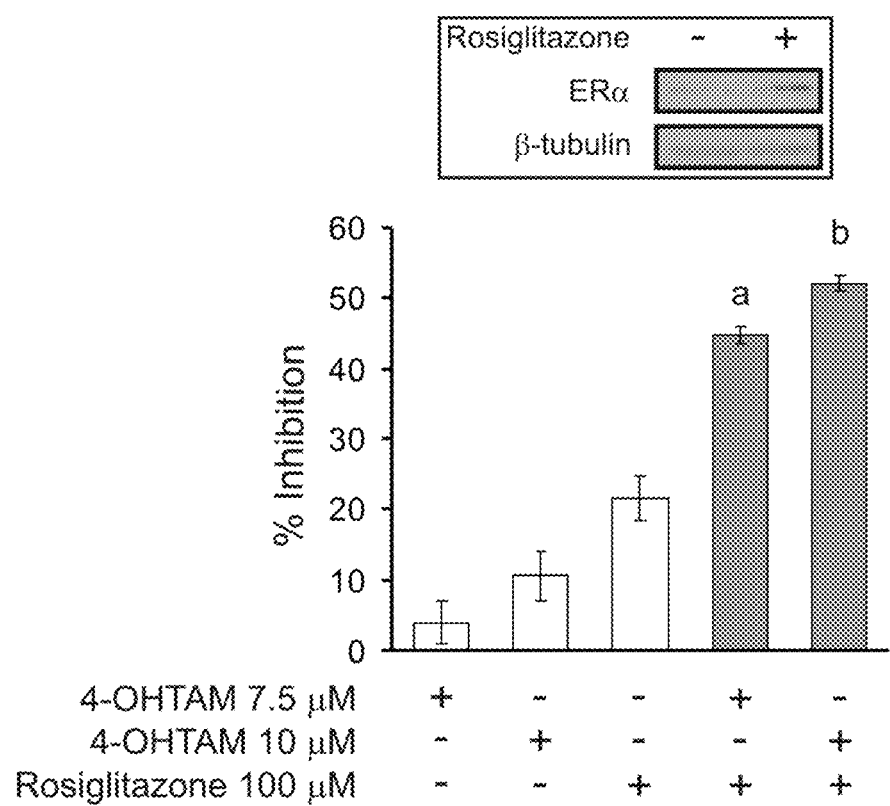

FIG. 7 shows the cell proliferation inhibition by combining sub-effective doses of ACSL4 and ER pathway inhibitors in MDA MB-231 cells. MDA-MB-231 cells were plated as described for MCF-7 Tet-Off/ACSL4 cells in FIG. 7 and then incubated with rosiglitazone (100 μM) and/or 4-hidroxitamoxifen (4-OHTAM 7.5 or 10 μM) for 96 h. Subsequently, cell proliferation was measured by BrdU incorporation assays. Data are presented as inhibition of cell proliferation compared to control cells. White bars indicate a single inhibitor treatment while grey bars indicate combined inhibitor treatment. Data are presented as means±SD. a and b:*** p<0.001 vs. corresponding single inhibitors. Inset: MDA-MB-231 cells were incubated in the presence or absence of rosiglitazone (100 μM) for 48 h. ERα protein levels were evaluated by Western blot and a representative blot is shown.

Figure 8:
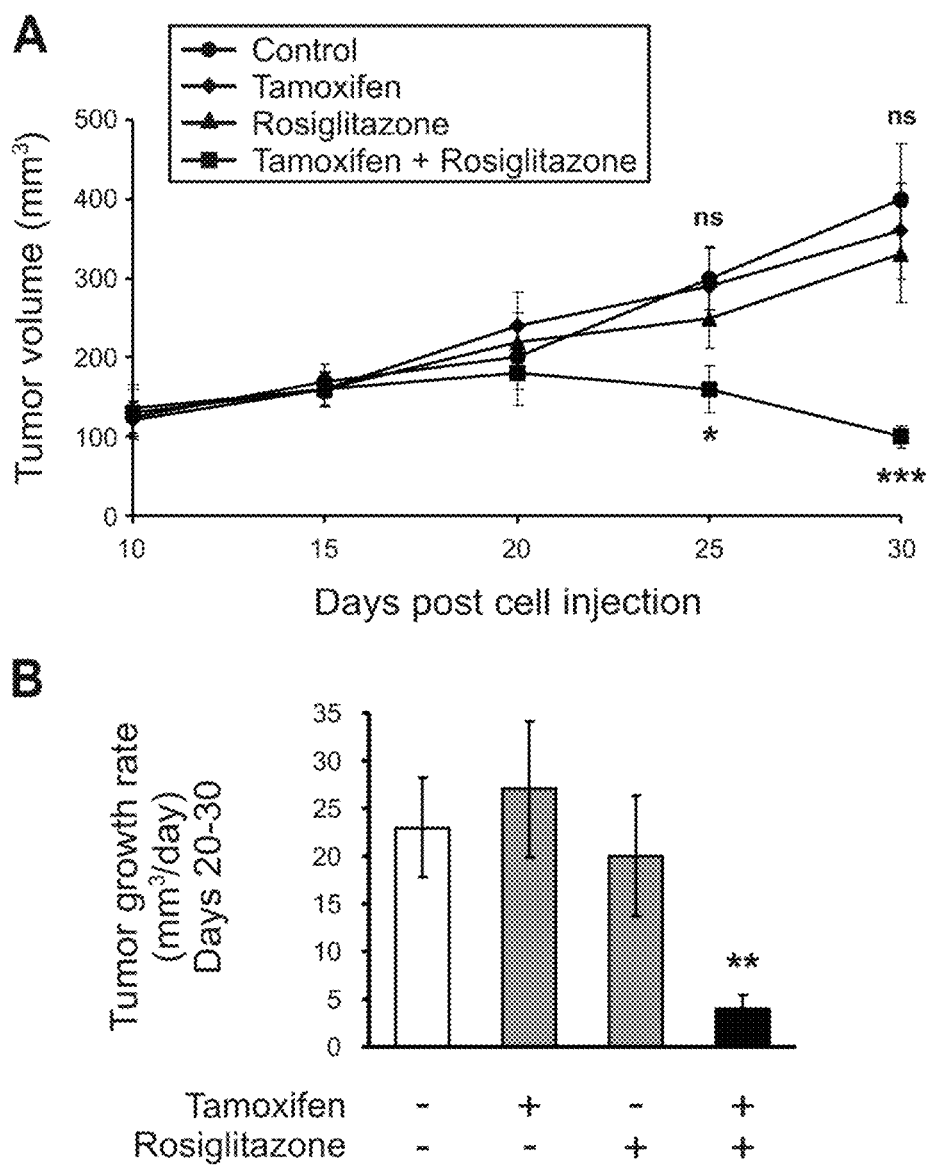

FIG. 8 shows the effect of ACSL4 and ER pathway inhibitors in the MDA-MB-231 human breast xenograft model. Mice bearing MDA-MB-231 tumor xenografts were treated with either vehicle (control), rosiglitazone or tamoxifen alone, or with a combination of the two inhibitors at the doses described herein for 25 consecutive days. Comparison of (A) average tumor volume and (B) tumor growth rate between days 20-30 was determined. Data are presented as means±SD, n=5. Asterisks indicate significant differences between tumor volumes by two-way ANOVA (A) and between tumor growth rates by one-way ANOVA (B). ns vs. single inhibitors; * p<0.05,  p<0.01, * p<0.001 vs. corresponding single inhibitors.

DETAILED DESCRIPTION OF THE INVENTION

The present application discloses that ACSL4 overexpression can trigger several different mechanisms to regulate the aggressiveness of breast cancer cells, including the pathways stimulated by growth factors, nutrients, cytokines and changes in energy metabolism. ACSL4 might be a novel regulator of mTOR; therefore, the combined inhibition of an upstream mechanism such as ACSL4 activity seems to be a potential target to be used in order to avoid compensatory feedback. And, as ACSL4 has been related to colon and hepatocellular carcinoma, besides breast carcinoma, the present findings suggest novel mediators, specifically for combined pharmacological treatment toward tumor growth inhibition.

The major findings of the present study are: (a) ACSL4 overexpression induces changes in genes associated with biofunctions; (b) the four biofunctions with the highest activation z-scores are: cellular movement, growth and proliferation, protein and cellular assembly and organization; (c) the biggest differences in phosphorylation patterns are observed in the signaling phosphoproteins working in pathways that trigger AKT, mTOR, p70S6K, S6 phosphorylation and GS3K, which is why ACSL4 can be considered a novel activator of the mTOR pathway, for both mTORC1 and mTORC2 targets, in growth factor and nutrient stimulus; (d) the inhibition of ACSL4 expression completely abolishes the changes observed in protein expression and phosphorylation-dephosphorylation, which demonstrates the specificity of ACSL4 function; (e) the pharmacological blockade of mTOR-p70S6K signaling activation inhibits ACSL4-induced cell proliferation; (j) ACSL4 inhibition and mTOR/ER inhibition exhibit synergistic behavior.

The term "synergistic" or "synergic", as used herein, is known by those skilled in the art, and refers to the joint action of agents, for example, drugs in a composition, that—taken together—produce a superior effect than the sum of their individual effects. That is, the combination of two or more active ingredients in a composition which is referred to as synergistic exerts a better effect than the sum of the separate effects of those two or more active ingredients individually.

ABBREVIATIONS

Throughout the present invention, the following abbreviations are used:
ER, estrogen-receptor-α
PR, progesterone-receptor
HER2, human epidermal growth factor 2 receptor
ACSL4, acyl-CoA synthetase 4
AA, arachidonic acid
4-OHTAM, 4-hydroxytamoxifen
RNA-Seq, RNA Sequencing
DAVID, Database for Annotation, Visualization and Integrated Discovery
IPA, Ingenuity Pathway Analysis
RPPA, Reverse Phase Protein Assay
FPKM, fragments per kilo base of exon model per million of reads mapped
IL20, interleukin 20
EHT, Ets Homologous factor
SP6, transcription factor (Krueppel-like factor 14)
TGFβ2, transforming growth factor beta 2
ERBB2, V-erb avian erythroblastic leukemia viral oncogene homolog 2
VEFGA, vascular endothelial growth factor A
ITGA2, integrin alpha 2
MARK1, MAP/Microtubule affinity-regulating kinase 1
FXYD5, FXYD domain containing ion transport regulator 5
RET, ret proto-oncogene
FOS, murine osteosarcoma viral oncogene homolog
FGFR1, fibroblast growth factor receptor 1
WNT6, Wingless-Type MMTV Integration Site Family Member 6
WNT10A, Wingless-Type MMTV Integration Site Family Member 10A
WIF1, WNT inhibitory factor 1
ULK1, Unc-51-like autophagy-activating kinase 1
RAI2, retinoic acid induced 2
miR, microRNA
PTEN, phosphatase and tensin homolog
AKT, V-Akt Murine Thymoma Viral Oncogene
EIF2, eukaryotic translation initiation factor 2
p70S6K, ribosomal protein S6 kinase 70 kDa polypeptide 1,
mTOR, mechanistic target of rapamycin
S6, ribosomal protein S6
mTORC1, rapamycin-nutrient-sensitive multiprotein complex
mTORC2, rapamycin-growth factor-sensitive nutrient-insensitive complex
TSC1, tuberous sclerosis 1
TSC2, tuberous sclerosis 2 or tuberin
ERK1/2, extracellular-signal-regulated kinase %
AKTS1, AKT1 Substrate 1 (Proline-Rich)

PRKAA1 (or AMPK), protein kinase AMP-activated alpha 1 catalytic subunit
FAK, focal adhesion kinase
GSK3α and GSK3β, glycogen synthase kinase-3 alpha and beta
FZD7, frizzled class receptor 7 (WNT receptor)
IGFBP2, insulin-like growth factor binding protein
ATM, ataxia telangiectasia
MDM2, oncogene E3 ubiquitin protein ligase
EEF2, eukaryotic translation factor 4E binding protein 1
GAB2, GRB2-associated binding protein 2
ACC, acetyl-CoA-carboxylase alpha and beta
SDHA, succinate dehydrogenase complex subunit A flavoprotein
DVL3, dishevelled segment polarity protein 3
PI3K, phosphatidylinositol-4,5-bisphosphate 3-kinase
TZDs, thiazolidinedione family of drugs.

As used herein, a "pharmaceutical composition" refers to a product that comprises one or more active ingredients and an optional carrier/excipient. The composition may comprise inert ingredients, as well as any product that results, directly or indirectly, from the combination, complexing or aggregation of any two or more ingredients, or from the dissociation of one or more of the ingredients, or from other types of reactions or interactions of one or more of the ingredients. In general, the pharmaceutical compositions are prepared by uniformly and intimately associating the active ingredient(s) with a liquid carrier/excipient or a finely divided solid carrier/excipient or both, and later, if desired, conforming the product in the desired formulation. In particular, according to the present invention, each active ingredient may be formulated with a suitable carrier/excipient, and after that, if desired, the formulations may be combined to form a single final preparation. Alternatively, each active principle may be formulated with a suitable carrier/excipient thus forming separate individual preparations, in order to administer them in a simultaneous or sequential way.

The pharmaceutical composition includes sufficient active compound to produce the desired effect on the progress or state of the disease. Therefore, the pharmaceutical compositions of the present invention comprise any composition prepared by mixing active compound(s) and at least one pharmaceutically acceptable carrier/excipient. By "pharmaceutically acceptable", it is meant that the carrier, diluent or excipient must be compatible with the other ingredients of the formulation and must not be harmful for its recipient.

The term "treatment" as used herein refers to any treatment of a condition or human disease and includes: (1) inhibiting the disease or condition, that is, deterring its development, (2) alleviating the disease or condition, that is, causing the regression of the condition, or (3) deterring the symptoms of the disease.

The term "to inhibit" includes its generally accepted meaning that includes "to restrict," "to alleviate," "to improve," and "to slow," "to deter or to invert the progression, severity or a resulting symptom." As used herein, the term "therapy", such as in "drug therapy" or in relation to any medical therapy, includes in vivo or ex vivo diagnostic and therapeutic techniques carried out in humans.

In general, the pharmaceutical compositions of the present invention can be administered by standard routes, such as by parenteral route (for example, intravenous, intravertebral, subcutaneous or intramuscular), oral, tracheal, bronchial, intranasal, pulmonary, buccal, rectal, transdermal or topical. The administration can be systemic, regional or local.

The types of pharmaceutical compositions that can be used include: tablets or pills, chewable tablets, capsules (including microcapsules), powders, powders for reconstitution, solutions, parenteral solutions, aerosol solutions, ointments (creams and gels), suppositories, suspensions, and other types described herein or that are evident for an expert in the field, from general knowledge of the art. The active principle(s), for example, can also be in the form of a complex including cyclodextrins, their ethers or esters.

The inhibitory compounds used in the present invention may be taken in suitable forms for administration by ordinary processes, using auxiliary or excipient substances such as liquid or solid ingredients, in powder, such as pharmaceutically usual liquids or solids and expanders, solvents, emulsifiers, lubricants, flavoring agents, pigments and/or buffering substances (buffers). Frequently used auxiliary or excipient substances include: magnesium carbonate, titanium dioxide, lactose, sucrose, sorbitol, mannitol and other sugars or sugar alcohols, talcum, lactoprotein, gelatin, starch, amylopectin, cellulose and its derivatives; animal and vegetable oils such as fish liver oil, sunflower, peanut or sesame, polyethylene glycol; and solvents such as sterile water and mono- or polyhydric alcohols such as glycerol; as well as disintegrating agents and lubricating agents such as magnesium stearate, calcium stearate, sodium stearyl fumarate and polyethyleneglycol waxes. Then, the mixture may be processed into granules or compressed into tablets.

Each active ingredient can be separately premixed with the other non-active ingredients, before being mixed to form a formulation or, alternatively, the active ingredients can be mixed together, before being mixed with the inert ingredients to form a formulation.

Soft gelatin capsules can be prepared with capsules that contain a mixture of the active ingredients of the invention, vegetable oil, fat, or other vehicles suitable for soft gelatin capsules. Hard gelatin capsules can contain granules of the active ingredients. Hard gelatin capsules can also contain the active ingredients with solid ingredients in powder, such as lactose, sucrose, sorbitol, mannitol, potato starch, cornstarch, amylopectin, cellulose derivatives or gelatin.

Units for rectal administration can be prepared (i) in the form of suppositories that contain the active substances mixed with a base of neutral fat; (ii) in the form of a rectal gelatin capsule that contains the active substance in mixture with a vegetable oil, paraffin oil or another vehicle suitable for rectal gelatin capsules; (iii) in the form of a ready-to-use microenema; or (iv) in the form of a dry microenema formulation to be reconstituted in a suitable solvent before its administration.

Liquid preparations can be prepared in the form of syrups, elixirs, drops or concentrated suspensions, for example, solutions or suspensions that contain the active principles and the remainder consists of for example, sugar or sugar alcohols, and a mixture of ethanol, water, glycerol, propylene glycol and polyethylene glycol, if desired, such liquid preparations can contain pigment agents, flavoring agent, preservatives, saccharin and carboxymethyl cellulose and other thickening agents. Liquid preparations can also be prepared in dry powder form, reconstituted with suitable solvent before their use. Solutions for parenteral administration can be prepared as the solution of a formulation of the invention in a pharmaceutically acceptable solvent, such as a sterile water solution or non-water solvent, as vegetable oil, esters of long-chain aliphatic acids or propylene glycol. These solutions can also contain stabilizers, preservatives and/or buffers. Solutions for parenteral administration can also be prepared as a dry preparation, reconstituted with a suitable solvent before their use.

The compositions of the invention to be applied topically on the skin or the scalp can be prepared in the form of ointments (creams or gels). In an embodiment of the invention, an oil emulsion is prepared in water to form a cream. The active compounds in powder form are dissolved in a suitable solvent, such as, for example, propylene glycol. The aqueous phase can alternatively include an alcohol or isopropanol, adding a thickener, for example, Carbomer 934 or 940. The oily phase preferably includes mineral oil, petroleum jelly, cetyl alcohol and/or stearyl alcohol. Emulsifiers which can be used are: polysorbate 80, sorbitan monostearate or others known in the art. Buffering agents, antioxidants and chelating agents may also be added to improve the characteristics of the formulation.

Preparations for topical administration can be prepared for delivery in an aerosol. In these cases, the inhibitory compounds can be admixed with known excipients for aerosol, such as saline solution, alcohol, or fatty acid derivatives, to enhance bioavailability if necessary.

Formulations are also supplied in accordance with the present invention as "kits" that comprise one or more containers that separately contain one or more of the ingredients of the pharmaceutical composition of the invention in a suitable carrier/excipient, for its co-administration. These containers may include indications for the use thereof, such as instructions for use, or a notification in the form prescribed by a governmental agency that governs the manufacture, use or sale of pharmaceutical products, whose notification reflects approval by the agency of the manufacture, use or sale for human use.

The terms "combination therapy" or "co-administration" are intended to embrace the administration of each active agent in a sequential way, in a system that will provide the beneficial effects resulting from the combination of drugs, and it is intended to embrace the co-administration of these agents in a substantially simultaneous way, such as in a single dose unit that has a fixed ratio of these ingredients, or in multiple dose units, separate for each active agent.

The amount of each active ingredient and the dosage system to treat a disease condition with the compounds and compositions of the invention depends on a variety of factors, including: age, weight, sex and medical condition of the patient, severity of the disease and route and frequency of administration, as well as the particular compound employed, so that it can vary widely.

According to the present invention the compositions contain an acyl-CoA synthetase 4 (ACSL4) inhibitor selected from rosiglitazone, troglitazone or pioglitazone wherein rosiglitazone may be in an amount of about 0.01 mg to about 20 mg, more suitably in a range of about 0.1 mg to about 5 mg and more preferably in a range of about 0.5 mg to about 2 mg per dose unit. Troglitazone may be may be in an amount of about 1 mg to about 600 mg, more suitably in a range of about 5 mg to about 400 mg and more preferably in a range of about 50 mg to 200 mg, per dose unit.

The compositions of the invention may contain an mTOR inhibitor selected from rapamycin, temsirolimus, everolimus, tacrolimus, deforolimus, pimecrolimus, olcorolimus, zotarolimus or umirolimus. Rapamycin may be in an amount ranging from 500 µg to 10 mg/60 kg per daily dose unit.

The compositions of the invention may contain an estrogen receptor (ER) inhibitor selected from: tamoxifen, bazedoxifene, lasofoxifene, ormeloxifene, raloxifene, clomifene, tamoxifen derivatives and analogs (such as 4-OH-tamoxifen, toremifene, afimoxifene, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen, 4-hydroxy-N-demethyl-tamoxifen). Tamoxifen may be in an amount ranging from 2 to 50 mg/60 kg per daily dose unit.

Materials and Methods

Materials

Dulbecco's modified Eagle medium (DMEM), penicillin-streptomycin solution and trypsin-EDTA were purchased from GIBCO, Invitrogen Corporation (Grand Island, N.Y., USA). Fetal calf serum was from PAA laboratories GmbH (Pasching, Austria). Doxycycline, 3-(4,5-dimethyl-2-thiazolyl)-2,5-diphenyl-2H-tetrazoliumbromide) (MTT) and 4-hydroxytamoxifen (4-OHTAM) were purchased from Sigma Chemical Co. (St. Louis, Mo., USA). Rapamycin was obtained from Cayman Chemical Company (Michigan, Ill., USA). GW9662 was obtained from Tocris Bioscience (Bristol, UK). Monoclonal mouse anti-GSK-3α/β and polyclonal rabbit anti-ERα antibodies were from Santa Cruz Biotechnology, Inc. (Dallas, Tex., USA). Polyclonal rabbit phospho-GSK-3α/β (Ser21/9), phospho-p70 S6 (Thr398) and phospho-S6 ribosomal protein (Ser235/236) antibodies were from Cell Signaling Technology (Boston, Mass., USA). Phospho-AKT (Ser473) and phospho-Rictor (Thr135) rabbit monoclonal antibodies were purchased from Cell Signaling Technology (Boston, Mass., USA).

Horseradish peroxidase-conjugated goat anti-rabbit and goat-anti-mouse secondary antibodies and Immun-Blot polyvinylidene fluoride membrane was from Bio-Rad Laboratories (Hercules, Calif., USA). Enhanced chemiluminescence (ECL) was from GE Healthcare (Buckinghamshire, UK). Direct-zol RNA kit was from Zymo Research (Irvine, Calif., USA). Sterile and plastic material for tissue culture was from Orange Scientific (Braine-l'Alleud, Belgium). 5-bromo-2'-deoxyuridine (BrdU) cell proliferation ELISA kit was from Roche Diagnostics, Basel, Switzerland). All other reagents were of the highest grade available.

Cell Culture

Human breast cancer cell lines MDA-MB-231, MCF-7 and T47D were generously provided by Dr. Vasilios Papadopoulos (Research Institute of the McGill University Health Centre, Montreal, Canada) and obtained from the Lombardi Comprehensive Cancer Center (Georgetown University Medical Center, Washington D.C., USA). The tetracycline-repressible MCF-7 cell lines, designated MCF-7 Tet-Off empty vector, and MCF-7 Tet-Off-induced repression of ACSL4, designated MCF-7 Tet-Off/ACSL4 were obtained previously in the laboratory (Maloberti P. M. et al., 2010).

For transfection of MDA-MB-231 and T47D, cells were seeded the day before and grown up to 80% confluence. Transfection was performed in Opti-MEM medium with Lipofectamine 2000 reagent (Invitrogen) using the pSUPER.retro plasmid (OligoEngine, Seattle, Wash., USA) containing ACSL4 shRNA (AAGATTATTCTGTGGATGA) (SEQ ID NO. 1) for the MDA-MB-231 cells and the pcDNA3.1(+) (Invitrogen) plasmid containing ACSL4 cDNA for the T47D cells. The respective empty vectors were used as controls. Transfection efficiency was estimated by counting fluorescent cells transfected with the pRc/CMVi [11] plasmid containing the enhanced form of green fluorescent protein. Forty-eight hours after transfection, cells were selected in media containing 500 µg/ml G418 and 1 µg/ml Puromycin for 1 month and then collected for biochemical and cellular assays. T47D and MDA MB 231 transfected cell lines were designated T47D-ACSL4, T47D empty vector, MDA MB 231 shRNAACSL4, and MDA MB 231 mock, respectively.

Quantitative Reverse Transcription-PCR (qRT-PCR)

MCF-7 Tet-Off empty vector and MCF-7 Tet-Off/ACSL4 total RNA was extracted using Tri-Reagent following the manufacturer's instructions. Any residual genomic DNA was removed by treating RNA with DNase I (15 min at room temperature), which was subsequently inactivated by incubation with 2.5 mM EDTA for 10 min at 65° C. Two µg of total RNA were reverse transcribed using random hexamers and M-MLV Reverse Transcriptase according to the manufacturers protocol.

For Real-Time PCR, gene specific primers were obtained from RealTimePrimers.com (Elkins Park, Pa., USA). Real-time PCR was performed using Applied Biosystems 7300 Real-Time PCR System. For each reaction, 20 µl of solution containing 5 µl of cDNA, 10 µM forward and reverse primers, and 10 µl of SYBR Select Master Mix was used. All reactions were performed in triplicate. Amplification was initiated by a 2-min preincubation at 50° C., 2-min incubation at 95° C., followed by 40 cycles at 95° C. for 15 sec, 55° C. for 15 sec and 72° C. for 1 min, terminating at 95° C. for the last 15 sec. Gene mRNA expression levels were normalized to human 18S RNA expression, performed in parallel as endogenous control. Real-time PCR data were analyzed by calculating the $2^{-\Delta\Delta Ct}$ value (comparative Ct method) for each experimental sample.

Cell proliferation assays were measured by the 5-bromo-2'-deoxyuridine (BrdU) incorporation and the MTT assays, as previously described (Maloberti P. M. et al., 2010, supra).

For all the experimental tests carried out in the present invention, data analysis was performed using GraphPad Prism Software 5.01 (La Jolla, Calif., USA). Statistical significance was determined by analysis of variance (ANOVA) followed by Tukey-Kramer Multiple Comparison Test. Tumor response to treatment was compared using two-way ANOVA.

Assays

Assay 1

Identification of ACSL4-Responsive Genes in MCF-7 Tet-Off/ACSL4 Cells Through Transcriptome Analysis A body of data accumulated in the past years indicates that the metabolism of AA is involved in the maintenance of survival and proliferative capacities of various types of normal and cancer cells and plays a role in tumor progression and vessel wall disease. Despite this evidence linking the action of ACSL4 to the development of various types of cancer including colon, hepatocellular carcinoma, prostate and breast cancer, very little is known regarding the mechanism by which ACSL4 influences these lesions. Because ACSL4 plays a crucial role in tumor growth, the inventors have undertaken a systematic study to identify genes with tumorigenesis capacity and elucidate the underlying signaling mechanism.

Toward understanding the capacity of ACSL4 in the regulation of tumorigenesis, the present inventors have previously reported the involvement of AA lipoxygenase and cyclooxygenase metabolites in the action of ACSL4 (Maloberti P. M. et al., 2010; Orlando U. D. et al., 2012) and, in the present invention, the focus was placed on the identification of ACSL4-responsive genes using the RNA-Seq in MCF-7 Tet-Off/ACSL4 compared with an MCF-7 Tet-Off empty vector.

For the sample preparation and sequencing using the RNA-Seq technology, total RNAs were extracted from each of the cell lines by Direct-zol RNA kit (Zymo Research, Irvine, Calif.). RNA quality was assessed by agarose gel electrophoresis (visual absence of significant 28S and 18S rRNA degradation) and by spectrophotometry. RNA-Seq was performed by Zymo Research facility performing PolyA enrichment of the RNA samples. HiSeq 2×50 by paired-end reads from RNA-Seq of a human normal-tumor pair samples were analyzed first using the TopHat and Cufflinks software. TopHat (v2.0.6) was utilized for alignment of short reads to GRCh37, Cufflinks (v2.0.2) for isoform assembly and quantification, and commeRbund (v2.0.0) for visualization of differential analysis. Default parameters were used. The RNA-Seq quality control was performed using Dispersion, Volcano, MA, Density, PCA, Scatter and Box plots.

The correlation between RNA-Seq and Real-Time PCR data of differential gene expression from MCF-7 Tet-Off/ACSL4 to MCF-7 Tet-Off empty vector cells was determined. A comparison of fold changes between RNA-Seq and real-time RT-PCR for each gene was performed, verifying that the real-time RT-PCR expression profiles were mostly in agreement with RNA-Seq data.

Results show a total of 26705366 RNA-Seq reads acquired from MCF-7 Tet-Off/ACSL4 and 22258811 reads acquired from MCF-7 Tet-Off empty vector. The sequence reads were then aligned to a human genome reference (GRCh37) using TopHat version 2.0.6, with results rendering 93.30% of the MCF-7 Tet-Off/ACSL4 reads and 92.90% of the MCF-7 Tet-Off empty vector reads as successfully mapped.

The resulting read alignments (file format: BAM) were then assembled through Cufflinks version 2.0.2 for isoform assembly and quantification, and commeRbund (v2.0.0) for visualization of differential analysis (default parameters were used).

Assay 2

Differential Gene Expression in MCF-7 Tet-Off/ACSL4 Cells

In turn, gene expression levels were determined by measuring the sum of fragments per kilo base of exon model per million of reads mapped (FPKM), analyzed in each exon. To acquire more accurate results, data were filtered out whenever estimated FPKM values in both MCF-7 Tet-Off/ACSL4 and MCF-7 Tet-Off empty vector samples were less than 1.0 (cf. an FPKM value of 0.05 is commonly set as the lowest boundary of expression level). Only loci that have a $\log_2$ (fold change)>2 between MCF-7 Tet-Off/ACSL4 and MCF-7 Tet-Off empty vector were considered.

Ultimately, it was observed that from 32247 successfully sequenced loci 3944 were significantly and differentially expressed in MCF-7 Tet-Off/ACSL4 samples. Among them, 2501 were up-regulated, and 1443 were down-regulated. ACSL4 gene was one of the genes taken as a control of its overexpression and, as expected, it was one of the genes showing major differences between MCF-7 Tet-Off/ACSL4 and MCF-7 Tet-Off empty vector.

To determine the characteristic chromosomal location of genes controlled by ACSL4 expression, the CROC program was used to examine the expression landscape by plotting the number of differentially expressed genes along the whole chromosomes. To this end, chromosome distribution patterns of differentially expressed genes and gene clusters of ACSL4-overexpressing cells were analyzed using the CROC program (http://metagenomics.uv.es/CROC) and the results were corrected by the method of multiple test correction by Benjamini & Hochberg. The minimum number of gene per cluster was 3 and the reference type of statistical analysis was by chromosome. Results revealed that chromosome distribution patterns varied greatly with respect to gene density and, in particular, chromosome 1 showed the highest gene density among genes mapped (data not shown). A total of 52 clusters were found—chromosome 1 showed the highest number of clusters—, while the number of genes in clusters was 181.

Assay 3
IPA Functional Analysis of ACSL4-Dependent Transcriptome Alterations in MCF-7 Tet-Off/ACSL4

To gain insights into biological cell properties, the Ingenuity Pathway Analysis (IPA) was used to rank enriched functional categories of gene networks relating to the transcripts regulated in ACSL4-responsive gene sets acquired from the RNA-Seq data. The high-scoring associated diseases and disorders are shown in Table 1 below, while cancer was the disease showing the lowest p value among diseases and disorders.

TABLE 1

Top-associated disease and disorders analyzed by IPA.

| Name of Disease and Disorders | p-value | # molecules |
|---|---|---|
| Cancer | 5.74E−07-0.0191 | 530 |
| Infectious Disease | 4.56E−05-0.0174 | 136 |
| Reproductive System Disease | 7.35E−05-1.87E−02 | 163 |
| Dermatological Diseases and Conditions | 8.42E−05-0.0141 | 74 |
| Endocrine System Disorders | 1.09E−04-0.0197 | 78 |

As a result, 390 top biofunctions were verified which are concerned with the ACSL4-induced transcriptome alteration in MCF-7 Tet-Off/ACSL4 cells.

The top significantly tumorigenesis-related biofunctions concerned with the ACSL4-induced transcriptome alteration in MCF-7 Tet-Off/ACSL4 cells were identified. Only p-value less than 0.01 calculated by right-tailed Fisher Exact Test were considered significant. IPA uses the activation z-score algorithm to make predictions. The z-score algorithm is designed to reduce the chance that random data will generate significant predictions.

In agreement with previous results (Maloberti P. M. et al., 2010; Orlando U. D. et al., 2012) regarding ACSL4 effect on cell proliferation, invasion and migration, the top three biofunctions which were IPA-predicted to be increased in RNA-Seq data were cell movement, migration and proliferation. Also, the genes regulated by ACSL4 within these top-three biofunctions (data not shown) were assessed by Ingenuity Pathway Analysis (IPA).

The top ten most significantly up-regulated functions related to gene networks in the RNA-Seq—along with a list of the corresponding genes in each function network—, were determined in the ACSL4-overexpressing cells (data not shown). The network corresponding to the top ten up-regulated functions was also outlined (not shown). Score was calculated as a negative exponent of p-value by a right-tailed Fisher Exact test (calculates the likelihood that the Network Eligible Molecules that are part of a network are found therein by random chance alone).

Assay 4
Analysis of Gene-Expression Changes Found in RNA-Seq Data and IPA by Real-Time RT-PCR On the basis of results obtained in RNA-Seq and IPA, 42 top genes were determined to exhibit differential changes when ACSL4 is overexpressed (as can be seen in Table 2 below), and further validated the gene-expression changes found in RNA-Seq data and IPA by real-time RT-PCR in independent biologic repeats of samples from MCF-7 Tet-Off/ACSL4 and MCF-7 Tet-Off empty vector under the same conditions used for RNA-Seq analysis.

For this analysis, total RNA was isolated from MCF-7 Tet-Off empty vector and MCF-7 Tet-Off/ACSL4 cells, reverse transcribed and subjected to Real-Time PCR using specific primers. Each transcript expression levels were normalized to mouse 18S RNA expression, performed in parallel as endogenous control.

TABLE 2

Identification of significantly up-regulated and down-regulated genes by ACSL4 overexpression using RNA-Seq.

| Name | Gene Symbol | Location | Type(s) |
|---|---|---|---|
| Genes upregulated | | | |
| De-etiolated homolog 1 (Arabidopsis) | DET1 | nucleus | other |
| NADPH oxidase 3 | NOX3 | cytoplasm | enzyme |
| Patched 2 | PTCH2 | plasma membrane | transmembrane receptor |
| Wingless-type MMTV integration site family, member 6 | WNT6 | extracellular space | other |
| Zinc finger, matrin-type 4 | ZMAT4 | nucleus | other |
| 2′-5′-oligoadenylate synthetase 1, 40/46 kDa | OAS1 | cytoplasm | enzyme |
| Cytochrome c oxidase subunit VIIb2 | COX7B2 | unknown | unknown |
| Interleukin 24 | IL24 | extracellular space | cytokine |
| Transforming growth factor, beta 2 | TGFB2 | extracellular space | growth factor |
| Interferon, alpha-inducible protein 6 | IFI6 | cytoplasm | other |
| Sp6 transcription factor | SP6 | nucleus | transcription regulator |
| Acyl-CoA oxidase 2, branched chain | ACOX2 | cytoplasm | enzyme |
| Zinc finger CCCH-type containing 15 | ZC3H15 | nucleus | other |
| Fibroblast growth factor 11 | FGF11 | extracellular space | other |
| FGFR1 oncogene partner | FGFR1OP | cytoplasm | kinase |
| Integrin, alpha 2 (CD49B, alpha 2 subunit of VLA-2 receptor) | ITGA2 | plasma membrane | transmembrane receptor |

TABLE 2-continued

Identification of significantly up-regulated and down-regulated genes by ACSL4 overexpression using RNA-Seq.

| Name | Gene Symbol | Location | Type(s) |
|---|---|---|---|
| Laminin, beta 1 | LAMB1 | extracellular space | other |
| Nuclear receptor coactivator 4 | NCOA4 | nucleus | transcription regulator |
| Phospholipase D1, phosphatidylcholine-specific | PLD1 | cytoplasm | enzyme |
| Ret proto-oncogene | RET | plasma membrane | kinase |
| FBJ murine osteosarcoma viral oncogene homolog | FOS | nucleus | transcription regulator |
| v-erb-b2 | ERBB2 | plasma membrane | kinase |
| Retinoic acid induced 2 | RAI2 | unknown | other |
| Dual specificity phosphatase 18 | DUSP18 | cytoplasm | phosphatase |
| Transcription factor B1, mitochondrial | TFB1M | cytoplasm | transcription regulator |
| MAP/microtubule affinity-regulating kinase 1 | MARK1 | cytoplasm | kinase |
| Interleukin 20 | IL20 | extracellular space | cytokine |
| Transglutaminase 1 | TGM1 | plasma membrane | enzyme |
| Fatty acyl CoA reductase 2 | FAR2 | cytoplasm | enzyme |
| Synaptotagmin XIII | SYT13 | plasma membrane | transporter |
| aldehyde oxidase 1 | AOX1 | cytoplasm | enzyme |
| G protein, alpha inhibiting activity | GNAI1 | plasma membrane | enzyme |
| FXYD domain containing ion transport regulator 5 | FXYD5 | plasma membrane | ion channel |
| Genes downregulated | | | |
| Protein tyrosine phosphatase, non-receptor type 22 | PTPN22 | Cytoplasm | phosphatase |
| Prickle homolog 2 | PRIKLE2 | Nucleus | other |
| ADAM metallopeptidase with thrombospondin type 1 motif, 9 | ADAMTS9 | Extracellular Space | peptidase |
| G antigen 8 | GAGE12B/GAGE8 | unknown | other |
| Neurotrophic tyrosine kinase, receptor, type 3 | NTRK3 | Plasma Membrane | kinase |
| Contactin associated protein-like 3B | CNTNAP3B | unknown | other |
| Deiodinase, iodothyronine, type II | DIO2 | Cytoplasm | enzyme |
| Zinc finger protein 217 | ZNF217 | Nucleus | transcription regulator |
| Ca++-dependent secretion activator | CADPS | Plasma Membrane | other |

The attention was next focused on categories that were relevant to this study, sub-grouped these genes by function and measured an example of each of them (i.e. cytokines, transcription factors, growth factors, integrin family and cytoskeleton, Wnt signaling family, oncogenes, growth factor receptors and energy metabolism). Most of these genes have central roles in the biology of cancer cells regarding proliferation, migration and invasion.

ACSL4 increased the expression levels of IL20, Ets homologous factor (EHT), SP6 transcription factor (Krueppel-like factor 14), transforming growth factor beta 2 (TGFβ2), V-erb avian erythroblast leukemia viral oncogene homologue 2 (ERBB2), vascular endothelial growth factor A (VEFGA), integrin alpha 2 (ITGA2), MAP/Microtubule affinity-regulating kinase 1 (MARK1), FXYD domain containing ion transport regulator 5 (FXYD5), ret proto-oncogene (RET), murine osteosarcoma viral oncogene homolog (FOS), fibroblast growth factor receptor 1 (FGFR1) and Wingless-Type MMTV Integration Site Family, Member 6 (WNT6) and WNT10A. One of the genes showing a marked decrease after ACSL4 expression was the WNT inhibitory factor 1 (WIF1).

IL20 has been demonstrated to be up-regulated in muscle-invasive bladder cancer patients, while EHT and SP6 are involved in differentiation and carcinogenesis. The SP6 has also been proposed to contribute to the malignant phenotype of breast tumors. TGFβ2, ERbB2, VEFGA, ITGA2, MARK1, FXYD5, RET and FOS are involved in tumor progression as well. Other genes measured included the Unc-51-like autophagy-activating kinase 1 (ULK1) and the retinoic acid induced 2 (RAI2). In short, most of the genes confirmed to be up-regulated here have well established roles in tumorigenesis.

In addition, Table 3 shows the top small nuclear RNA and microRNA (miR) regulated by ACSL4. MicroRNAs play an important role in virtually all biological pathways and they may hence influence numerous cancer-relevant processes. ACSL4 up-regulates miR-29a, whose overexpression has been described to increase tube formation and migration in endothelial cultures.

TABLE 3

Top small nuclear RNA and microRNA regulated by ACSL4.

| | Gene Symbol | Location | Change |
|---|---|---|---|
| Small nuclear RNA (some examples) | | | |
| RNA, U12 small nuclear | RNU12 | Nucleus | Upregulated |
| RNA, U4 small nuclear 1 | RNU4-1 | Nucleus | Upregulated |
| RNA, U4atac small nuclear (U12-dependent splicing) | RNU4ATAC | Nucleus | Upregulated |
| RNA, U5A small nuclear 1 | RNU5A-1 | unknown | Upregulated |
| RNA, U5D small nuclear 1 | RNU5D-1 | unknown | Upregulated |

TABLE 3-continued

Top small nuclear RNA and microRNA regulated by ACSL4.

| | Gene Symbol | Location | Change |
|---|---|---|---|
| RNA, U5E small nuclear 1 | RNU5E-1 | unknown | Upregulated |
| small nucleolar RNA, H/ACA box 8 | SNORA4 | unknown | Downregulated |
| Micro RNA (some examples) | | | |
| microRNA 29a | miR-29 | Cytoplasm | Upregulated |
| microRNA 1290 | miR-1290 | Cytoplasm | Upregulated |
| microRNA 25 | miR-25 | Cytoplasm | Downregulated |
| microRNA let-7a-1 | let-7 | Cytoplasm | Downregulated |
| microRNA let-7d | let-7 | Cytoplasm | Downregulated |

Overall, the RNA-Seq and IPA have identified genes that could potentially play important roles in the regulation of invasion and migration of breast tumor cells in vivo.

IPA analysis of the RNA-Seq towards canonical pathways. The pathways that were designated significantly enriched by the software, with a p-value<0.05 by Fisher's Exact test, are shown in Table 4.

Eukaryotic translation initiation factor 2 (EIF2), protein ubiquitination, ribosomal protein S6 kinase 70 kDa polypeptide 1 (p70S6K), mechanistic target of rapamycin (mTOR) and the signaling of molecular mechanisms of cancer are among the top canonical pathways triggered by ACSL4 with the lowest p-values.

TABLE 4

Enriched canonical pathways in ACSL4-overexpressing MCF-7 cells.

| Ingenuity Canonical Pathways | -log(p-value) |
|---|---|
| EIF2 Signaling | 21.2 |
| Protein Ubiquitination Pathway | 14.6 |
| Regulation of eIF4 and p70S6K Signaling | 8.88 |
| Molecular Mechanisms of Cancer | 8.26 |
| mTOR Signaling | 8.18 |
| Mitochondrial Dysfunction | 7.47 |
| NRF2-mediated Oxidative Stress Response | 6.88 |
| ATM Signaling | 6.81 |
| Hypoxia Signaling in the Cardiovascular System | 6.67 |
| Oxidative Phosphorylation | 6.25 |
| PI3K/AKT Signaling | 6.19 |
| 14-3-3-mediated Signaling | 5.72 |
| NGF Signaling | 5.50 |
| PTEN Signaling | 5.14 |
| Antiproliferative Role of TOB in T Cell Signaling | 5.12 |
| Pancreatic Adenocarcinoma Signaling | 4.94 |
| D-myo-inositol (1,3,4)-trisphosphate Biosynthesis | 4.76 |
| ERK5 Signaling | 4.66 |
| Type II Diabetes Mellitus Signaling | 4.66 |
| Hereditary Breast Cancer Signaling | 4.55 |
| TGF-β Signaling | 4.55 |

Assay 5
An ACSL4 Functional Proteomic Signature of MCF-7 Tet-Off/ACSL4 Cells

In order to study the signaling pathway triggered by ACSL4 on the basis of RNA-Seq bioinformatics studies showed in Table 4, a functional protein signature of the ACSL4 pathway was next defined by using the reverse phase protein array (RPPA), a high-throughput antibody-based technique developed for functional proteomic studies to measure phosphorylation states, as well as total levels of key signaling pathway intermediaries.

The RPPA assay was performed in the RPPA Core Facility—Functional Proteomics from MD—Anderson Cancer Center, University of Texas, USA. Cellular proteins were denatured by 1% SDS (with β-mercaptoethanol) and diluted in five 2-fold serial dilutions in dilution buffer (lysis buffer containing 1% SDS). Serial diluted lysates were arrayed on nitrocellulose-coated slides (Grace Biolab) by Aushon 2470 Arrayer (Aushon BioSystems). Total 5808 array spots were arranged on each slide including the spots corresponding to positive and negative controls prepared from mixed cell lysates or dilution buffer, respectively. Each slide was probed with a validated primary antibody plus a biotin-conjugated secondary antibody. Only antibodies with a Pearson correlation coefficient between RPPA and western blotting greater than 0.7 were used in RPPA studies. Antibodies with a single or dominant band on western blotting were further assessed by direct comparison to RPPA using cell lines with differential protein expression or modulated with ligands/inhibitors or siRNA for phospho- or structural proteins, respectively. The signal obtained was amplified using a Dako Cytomation-catalyzed system (Dako) and visualized by DAB colorimetric reaction. The slides were scanned, analyzed, and quantified using a customized-software Microvigene (VigeneTech Inc.) to generate spot intensity. Each dilution curve was fitted with a logistic model ("Supercurve Fitting" developed by the Department of Bioinformatics and Computational Biology in MD Anderson Cancer Center, "http://bioinformatics.mdanderson.org/OOMPA"). This fits a single curve using all the samples (i.e., dilution series) on a slide with the signal intensity as the response variable and the dilution steps as independent variables. The fitted curve is plotted with the signal intensities—both observed and fitted—on the y-axis and the log 2-concentration of proteins on the x-axis for diagnostic purposes. The protein concentrations of each set of slides were then normalized by median polish, which was corrected across samples by the linear expression values using the median expression levels of all antibody experiments to calculate a loading correction factor for each sample. A total of 217 different antibodies (not shown) were used in the RPPA analysis which were either directed to signaling proteins or directed to specific phosphorylated sites known to regulate protein signaling activity. The analysis was performed on lysates derived from MCF-7 Tet-Off/ACSL4, MCF-7 Tet-Off empty vector and doxycycline-treated MCF-7 Tet-Off/ACSL4 cells, the latter used to specifically override ACSL4 expression.

The pattern of protein expression and/or phosphorylation was remarkably different between MCF-7 Tet-Off/ACSL4 and MCF-7 Tet-Off empty vector. Lysates from doxycycline-treated MCF-7 Tet-Off/ACSL4 cells showed a pattern similar to that of MCF-7 Tet-Off empty vector, further supporting the role of ACSL4 in the effects observed.

Figure 1:
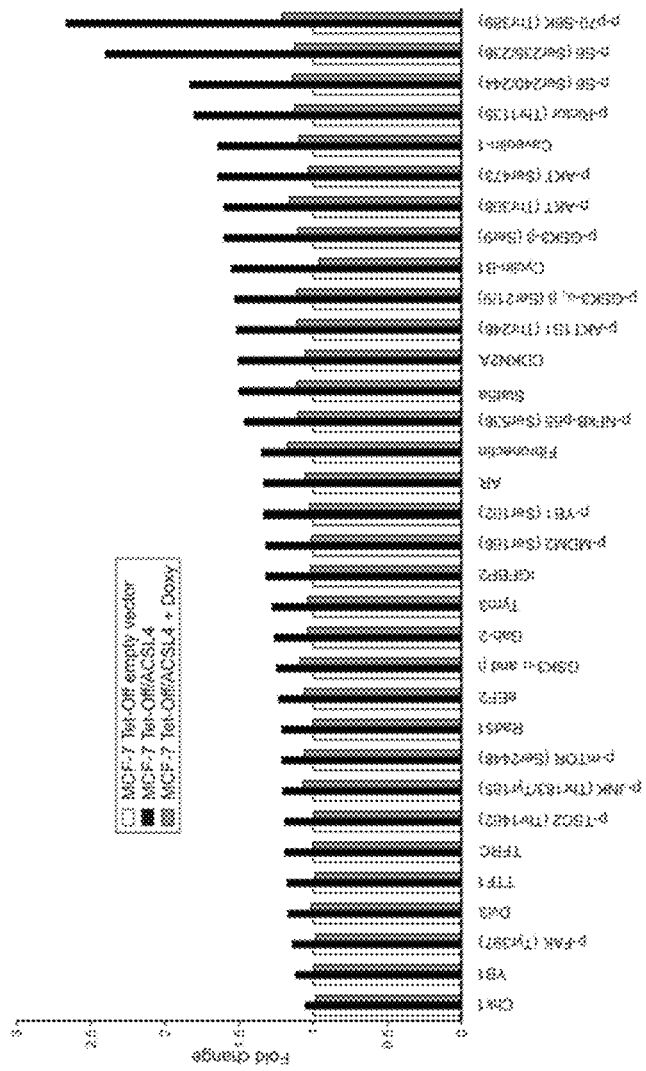
FIG. 1 shows the identification of significantly up-regulated protein expression or phosphorylation in ACSL4-overexpressing cells using RPPA. Data is presented as fold change.
Figure 2:
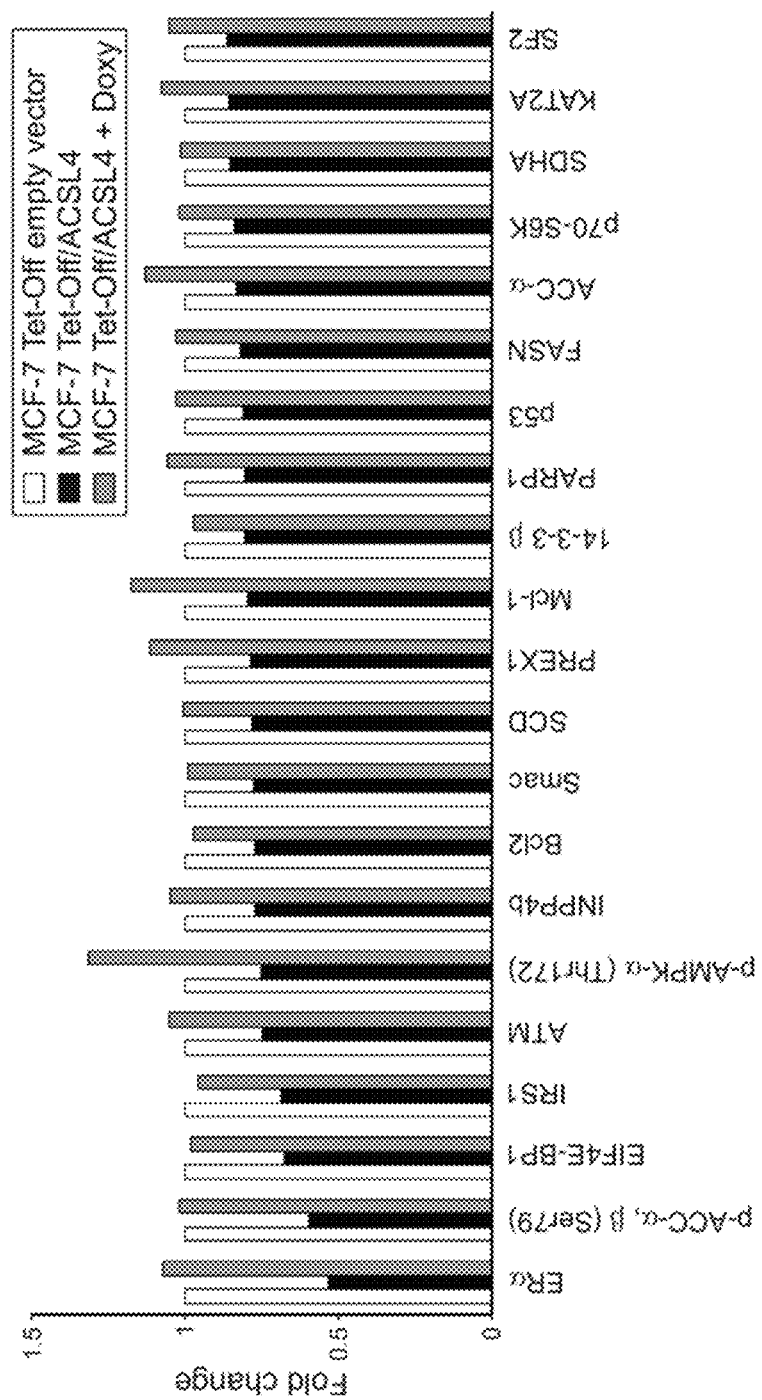
FIG. 2 shows the identification of significantly down-regulated protein expression or phosphorylation in ACSL4-overexpressing cells using RPPA. Data is presented as fold change.

Proteins were extracted from MCF-7 Tet-Off empty vector, MCF-7 Tet-Off/ACSL4 cells, and doxycycline treated-MCF-7 Tet-Off/ACSL4 (Doxy, 1 ug/ml, 48 h) cells, and were subjected to RPPA analysis as described in the present Example. FIGS. 1 and 2 show the proteins that exhibited a significant increase or decrease, respectively, in expression or phosphorylation status. ACSL4 overexpression in MCF-7 breast cancer cells changed the pattern of expression or the pattern of phospho-dephosphorylation of about fifty proteins. These effects were reversed by doxycycline treatment, which confirms the specificity of the functional-proteomic signature of ACSL4.

Assay 6
Functional Annotation Analysis Using DAVID Bioinformatics Software on RPPA Data Next, a functional annotation analysis was performed, using the bioinformatics program DAVID (Database for Annotation, Visualization and Integrated Discovery) on the basis of RPPA data.

DAVID (http://david.abcc.ncifcrf.gov/) and Ingenuity Pathways Analysis (IPA; Ingenuity Systems, Inc) were used in order to identify the statistically significant biological functions, and signaling pathways affected by the genes differentially expressed in the comparisons. IPA is the largest curated database and analysis system for understanding the signaling and metabolic pathways, molecular networks, and biological processes that are most significantly changed in a dataset of interest (http://www.ingenuity.com).

Ranking and significance of the biofunctions and the canonical pathways were tested by the p-value. Additionally, canonical pathways were ordered by the ratio (number of genes from the input data set that map to the pathway divided by the total number of molecules that exist in the canonical pathway). IPA also generated cellular networks where the differentially regulated genes can be related according to previously known associations between genes or proteins, but independently of established canonical pathways. Top networks represented associative network functions based on a score that considers the −log (p-value), which aggregates the likelihood of the genes in the network being found together due to random chance.

By means of functional annotation analysis of RPPA data from ACSL4-overexpressing MCF-7 cells using the bioinformatic program DAVID (data not shown), it was determined that insulin, mTOR and ERBB signaling and cancer pathways are the terms with the lowest p-values.

Enriched terms of KEGG_PATHWAY database were used for the functional annotation analysis. The p-value is calculated as modified Fisher Exact p-value, for gene-enrichment analysis. It ranges from 0 to 1. Fisher Exact p-value=0 represents perfect enrichment. Usually p-value is equal or smaller than 0.05 to be considered strongly enriched in the annotation categories. % refers as percentage of number of genes involved over total of genes in the term.

The DAVID scheme of pathways in cancer was outlined (not shown).

ACSL4 overexpression stimulated the dephosphorylation of two proteins and the phosphorylation of thirteen proteins, among them, which the phosphorylation of p70S6K on Thr389 and ribosomal protein S6 on Ser235/237 and 240/244 were markedly stimulated.

Figure 3:
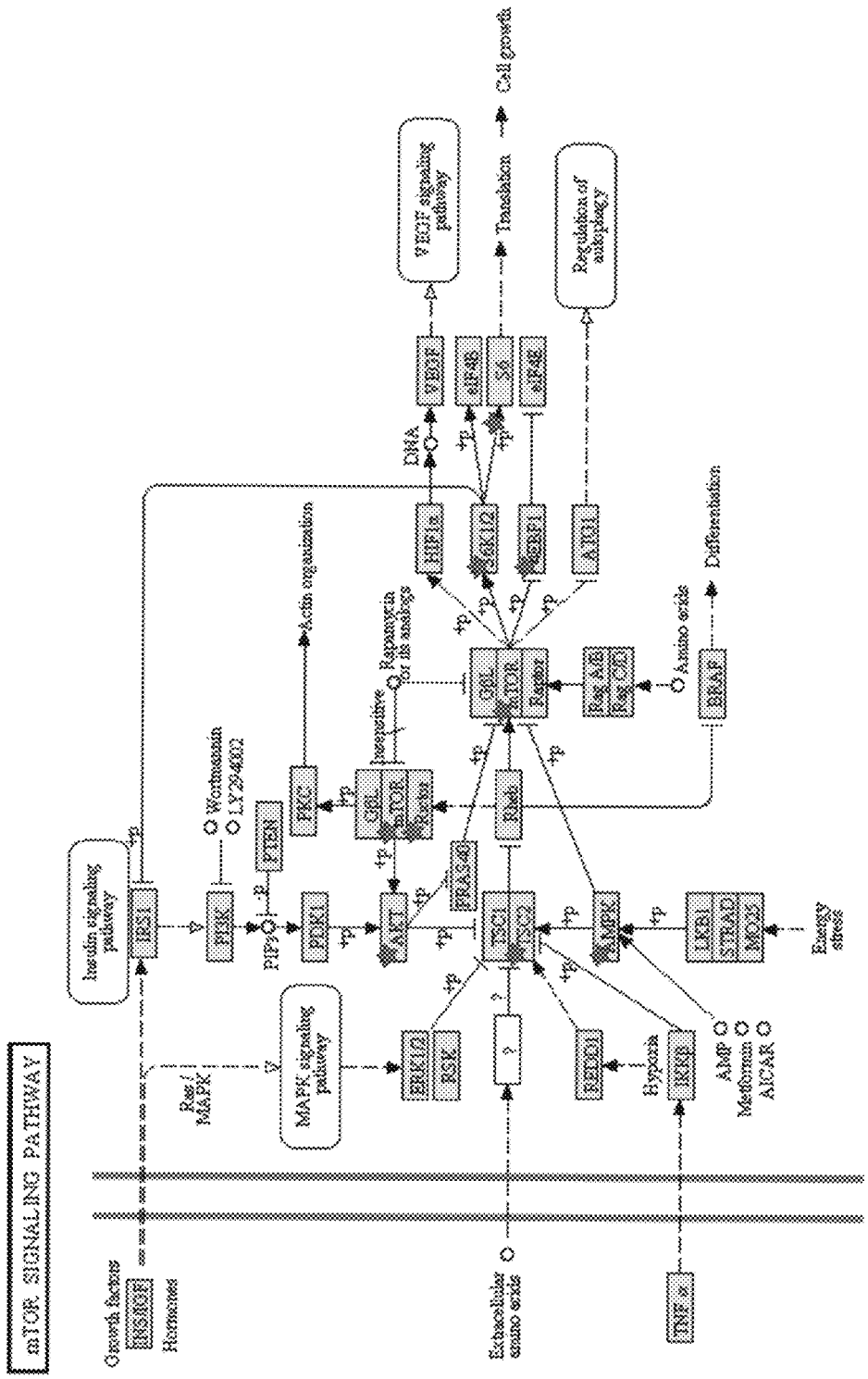
FIG. 3 shows the ACSL4 and mTOR signaling pathway. Star marks highlight ACSL4-regulated genes in RPPA analysis. The pathway scheme was obtained from KEGG_PATHWAY database. Analysis was performed by DAVID bioinformatics tool.

Together with the increase in S6 phosphorylation, ACSL4 overexpression also enhanced the phosphorylation of mTOR on Ser2448 without changes in protein levels (FIG. 3). mTOR has emerged as a critical effector in cell-signaling pathways commonly deregulated in human cancer. mTOR is regulated by growth factors and nutrients, which indicates that it is at the interface of two different growth signals, and comprises a rapamycin- and nutrient-sensitive multiprotein complex (mTORC1) and a growth factor-sensitive nutrient-insensitive complex (mTORC2). The mTORC1 pathway integrates input from at least five major intracellular and extracellular cues—growth factors, stress, energy status, oxygen and amino acids—to control numerous major processes including protein and lipid synthesis and autophagy.

mTORC1 has both upstream and downstream regulators. The heterodimer consisting of tuberous sclerosis 1 (TSC1) and tuberin (TSC2) is a key negative upstream regulator and functions as a GTPase-activating protein for the Ras homolog enriched in brain (Rheb) GTPase. This TSC1/TSC2 complex is phosphorylated and thus inactivated by several mechanisms—including AKT, extracellular-signal-regulated kinase 1/2 (ERK1/2) and p70S6K—and therefore activates mTORC1. AKT also participates in mTORC1 activation in an independent fashion by phosphorylating AKT1 Substrate 1 (Proline-Rich), named AKTS1, causing its dissociation from Raptor and suppressing mTORC inhibition.

An important enhancement in the phosphorylation of AKT on Ser308 and 473, and in the phosphorylation of the AKTS1 on Thr246 was observed. AKTS1 is a subunit of mTORC1, which regulates cell growth and survival in response to nutrient and hormonal signals. In addition, ACSL4 overexpression stimulated the abundance of Rictor, a subunit of mTORC2, which also regulates cell growth and survival in response to hormonal signals. mTORC2 is activated by growth factors but, in contrast to mTORC1, seems to be nutrient-insensitive. In other words, the ACSL4-functional proteomic signature obtained correlates with the ingenuity canonical pathways (Table 4) obtained with the ACSL4-transcriptome signature, where the AKT-mTOR-p70S6K signaling pathway seems to be one of the most important ACSL4 signatures.

Another interesting phosphoprotein that is modulated by ACSL4 overexpression is the protein encoded by gene PRKAA1 (AMPK or protein kinase, AMP-activated, alpha 1 catalytic subunit). When phosphorylated, this phosphoprotein negatively regulates the mTORC1 complex by phosphorylating its Raptor component and phosphorylating and activating TCS2. ACSL4 overexpression reduces the phosphorylation levels of this phosphoprotein on Thr172, decreasing its activity and inactivating the TCS2 complex. These results reinforce the participation of mTORC1 in ACSL4 signature.

It is known that both in normal and transformed cells the focal adhesion kinase (FAK) increases cell motility. This effect is activated by FAK phosphorylation on Tyr397, an event in turn enhanced by ACSL4 overexpression. FAK protein expression is elevated in many highly malignant human cancer types, and studies have shown that FAK signaling can promote changes in cell shape and the formation of podosomes or invadopodia, which in turn leads to an invasive cell phenotype.

In accordance with the results mentioned above, ACSL4 overexpression also stimulates the expression of caveolin. Caveolin-1 is a ubiquitously expressed scaffolding protein which is enriched in caveolae—i.e. subtypes of lipid rafts—and which is involved in several cellular functions such as endocytosis, vesicular transport and signal transduction. Studies also revealed that caveolin-1 is an essential regulator of the invadopodia-mediated degradation of extracellular matrix, which indicates that caveolin-1 plays an essential role in cancer cell invasion. Indeed, at least in breast cancer cell lines, caveolin-1 expression is predominantly observed in invasive cell lines and well correlated with invadopodia activity. The results correlate with those obtained in RNA-Seq, where cell movement showed the highest score (data not shown).

Glycogen synthase kinase-3 alpha and beta (GSK3α and GSK3β), critical negative regulators of diverse signaling pathways, are two additional phosphoproteins whose levels exhibit an important increase in response to ACSL4 overexpression, and whose phosphorylation on Ser21 and Ser9, respectively, inhibits GSK3 activity. GSK3β has also been implicated in the negative regulation of FAK activity.

As GSK3α has been shown to inhibit the Wnt signaling pathway, the inhibition of GSK3α activity by phosphorylation might suggest that Wnt signaling is part of the mechanism of action of ACSL4 overexpression. The aberrant regulation of the Wnt signaling pathway is a prevalent theme in cancer biology. From early observations that WNT overexpression could lead to malignant transformation of mouse mammary tissue to the most recent genetic discoveries gleaned from tumor genome sequencing, the Wnt pathway continues to evolve as a central mechanism in cancer biology. Results from RNA-Seq also show that ACSL4 overexpression causes a strong reduction in the expression of WIF1. The protein encoded by this gene inhibits WNT proteins, which are extracellular signaling molecules playing a role in embryonic development.

Mammary cancer is a prominent example involving the Wnt pathway, particularly cancers classified as basal-like or triple-negative and the expression of Wnt receptor FZD7 is characteristic of these types of breast cancer. Accordingly, Yang et al. recently reported experiments in which knockdown of FZD7, in cell line models of triple-negative breast cancer, reduced the expression of WNT target genes, inhibited tumorigenesis in vitro and greatly retarded the capacity of the MDA-MD-231 cell line to form tumors in mice (Yang et al., 2011). These results suggest that WNT ligands might drive certain breast cancers and are consistent with previous work from the Hynes laboratory. In agreement with these data, ACSL4 overexpression increased the expression of WNT6 and WNT10A (data not shown).

The WNT6 gene is overexpressed in cervical cancer cell lines and strongly co-expressed with another family member, WNT10A, in a colorectal cancer cell line. WNT6 overexpression may play a key role in carcinogenesis and is clustered with WNT10A in chromosome 2q35 region. The Wnt pathway is also implicated in the activation of mTORC1 through TSC1/2. In the studies carried out herein, Wnt signaling inhibited GSK3β, which normally phosphorylates and promotes TSC2 activity, and ACSL4 overexpression produced the stimulation of GSK3β on Ser9, which suggests that this mechanism of mTORC1 activation is also used by ACSL4.

As mentioned above, ACSL4 overexpression increases the phosphorylation of GSK3α and β. A requirement for ACSL4 has recently been demonstrated in dorsoventral patterning of zebrafish embryo and embryogenesis and neurogenesis in *Drosophila*. These results showed that ACSL4 works through the inhibition of AKT-dependent GSK3 activity by increasing its phosphorylation. And, given the interplay between morphogenetic signals in developing embryos, the interaction of these pathways might be expected in cancer.

ACSL4 overexpression also stimulates the protein levels of growth factors and their receptors, such as the insulin-like growth factor binding protein (IGFBP2).

Among genes involved in cell cycle control, ACSL4 decreases the level of the ataxia telangiectasia (ATM) gene. This protein is a kinase that regulates cell-cycle checkpoints by phosphorylating multiple proteins, including histone H2AX, CHK1 and CHK2 kinases and p53. ATM is activated through auto- or trans-phosphorylation on Ser1981 and/or Ser1893 in response to DNA damage, particularly the induction of DNA double-strand breaks. ATM signaling in RNA-Seq canonical pathway is within the top ten pathways (Table 4).

ACSL4 also produces a substantial increase in cyclin-B1, the oncogene E3 ubiquitin protein ligase (MDM2), the eukaryotic translation factor 4E binding protein 1 (EEF2) and the GRB2-associated binding protein 2 (GAB2). In the energy area, genes regulated are the acetyl-CoA-carboxylase alpha and beta (ACC) and the succinate dehydrogenase complex subunit A flavoprotein (SDHA), a part of the respiratory chain. ACC participate in fatty acid synthesis and oxidation and are phosphorylated by AMPK on Ser79 to inhibit their activity. ACSL4 overexpression decreases the activity of AMPK and thus decreases the phosphorylation of ACC.

Another gene increased by ACSL4 is the dishevelled segment polarity protein 3 (DVL3), a member of a multigene family which bears strong similarities with the *Drosophila* dishevelled gene, which encodes a cytoplasmic phosphoprotein that regulates cell proliferation.

Assay 7

Western Blot Analysis of the mTOR Pathway

Figure 4:
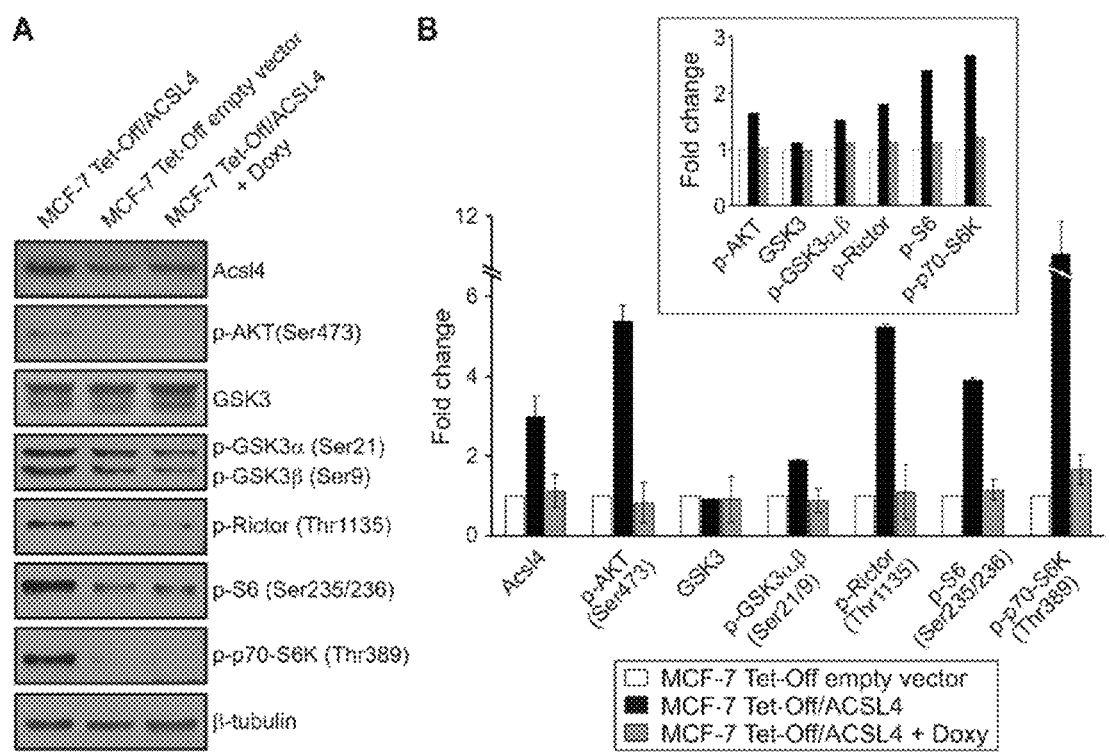
FIG. 4 shows Western blot analysis of mTOR pathway. A: Western blot was performed as previously described (Maloberti P. M. et al., 2010) using the indicated antibodies and the appropriate dilutions of primary antibodies were used as recommended by the manufacturer. Representative blots are shown. B: The integrated optical density of protein levels was quantified and normalized with the corresponding β-tubulin signal. Data represent the fold change means±SD of three independent experiments. Data is presented as mean±SD. Insert: RPPA data of the Western blot-validated proteins is shown as fold change.

Considering previous results indicating that ACSL4 might be a novel regulator of mTOR, Western blot analyses as described previously (Maloberti P. M. et al., 2010) were then performed, using six antibodies corresponding to the phosphorylation patterns of this pathway (FIG. 4). Appropriate dilutions of primary antibody were used as recommended by the manufacturer.

Whole cell extracts were obtained as described for the RPPA analysis (see Assay 5) from MCF-7 Tet-Off empty vector, MCF-7 Tet-Off/ACSL4, and doxycycline treated-MCF-7 Tet-Off/ACSL4 cells (Doxy, 1 ug/ml, 48 h).

All the antibodies used confirmed the results obtained by RPPA. As expected, an increase can be observed in the signaling pathway triggered by the phosphorylation of AKT-mTOR-p70S6K and S6 (FIG. 4, insert). In addition, an increase is also observed in the phospho-GSK3, as shown in RPPA.

To further assess the role of ACSL4 in the expression or post-translational modification of proteins, MCF-7 Tet-Off/ACSL4 cells were treated with doxycycline and cell extracts were prepared. Equal amounts of protein from MCF-7 Tet-Off/ACSL4 cells and cells treated with doxycycline were analyzed for RPPA and Western blot. As expected, the treatment of MCF-7 Tet-Off/ACSL4 cells with doxycycline resulted in the inhibition of the effect observed with the overexpression of ACSL4 (FIGS. 1 and 4).

EXAMPLES

The invention is further illustrated by the following Examples, which are not intended to limit the scope thereof. Instead, the examples set forth below should be understood only as exemplary embodiments for better taking into practice the present invention.

Example 1

Inhibition of Cell Proliferation Through the Combination of Sub-Effective Doses of ACSL4 and mTOR Inhibitors To further analyze pathway sequential activation, the effect of rapamycin, a specific inhibitor of mTOR which is an immediate downstream effector of AKT and upstream regulator of p70S6K, was also tested both alone and in combination with rosiglitazone—an inhibitor of ACSL4— on MCF-7 Tet-Off/ACSL4 cells.

MCF-7 Tet-Off empty vector and MCF-7 Tet-Off/ACSL4 cells were plated at a density of 4000 cells/well in 96-well plates with 10% FBS-supplemented D-MEM medium and allowed to adhere overnight at 37° C. in a humidified, 5% $CO_2$ atmosphere. The medium was then changed to serum-free medium. After 24 h, the cells were switched to 10%

FBS-supplemented D-MEM medium and incubated with rapamycin (10 nM) and/or rosiglitazone (75 μM) for 96 h. Subsequently, cell proliferation was measured by the bromodeoxyuridine (BrdU) incorporation assay.

Rosiglitazone and rapamycin were first tested alone at the concentrations used, and then in combination.

As mentioned before herein, by using the MCF-7 Tet-Off system, the present inventors have previously shown that the minimal dose of rapamycin for exerting significant inhibitory effects was 100 nM.

Figure 5:
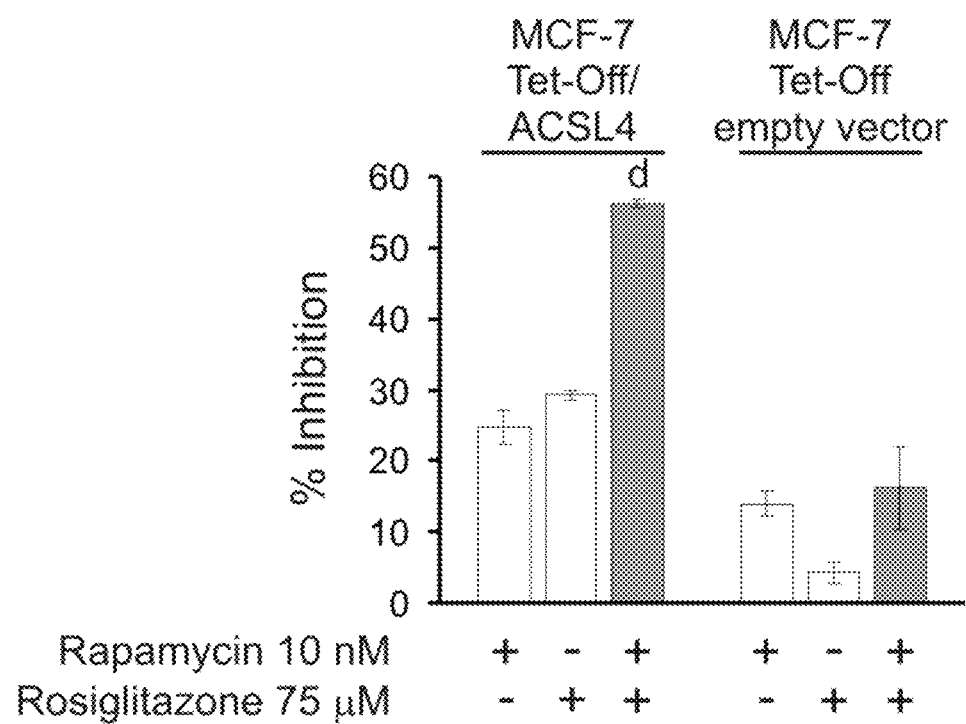
FIG. 5 shows the inhibition of cell proliferation through the combination of sub-maximal doses of ACSL4 and mTOR inhibitors. MCF-7 Tet-Off empty vector and MCF-7 Tet-Off/ACSL4 cells were incubated with rapamycin (10 nM) and/or rosiglitazone (75 μM) for 96 h. Subsequently, cell proliferation was measured by the bromo-deoxyuridine (BrdU) incorporation assay. Data is presented as percent inhibition of cell proliferation compared to control cells. White bars indicate a single inhibitor treatment while grey bars indicate a combined treatment with inhibitors. Data is presented as mean±SD. d:***p<0.001 vs. single inhibitors.

Treatment with sub-effective doses of rapamycin (10 nM) showed a significant inhibition of MCF-7 Tet-Off/ACSL4 cell proliferation, although it only reached 25% (FIG. 5). In turn, rapamycin and rosiglitazone together produced a combined synergic effect in the inhibition of cell proliferation. At the doses used, rapamycin and rosiglitazone had very little effect on the proliferation of the MCF-7 Tet-Off empty vector, which is in agreement with the low levels of the mTORC pathway and ACSL4.

|  | % inhibition of cell proliferation | | |
| --- | --- | --- | --- |
|  | Rosiglitazone 75 μM | Rapamycin 10 nM | Rapamycin 10 nM + Rosiglitazone 75 μM |
| MCF7 Tet-Off/ACSL4 - SD | 28.529 | 22.159 | 55.559 |
| MCF7 empty vector - SD | 2.813 | 12.211 | 10.347 |

On the basis of these results, ACSL4 is a potential therapeutic target, which can be used in combination with other inhibitors, thus preventing the side effects of supramaximal doses (Gelmon K. et al. Targeting triple-negative breast cancer: optimising therapeutic outcomes, Ann Oncol 23, 2223-2234; Yardley D. A., 2013, Combining mTOR Inhibitors with Chemotherapy and Other Targeted Therapies in Advanced Breast Cancer: Rationale, Clinical Experience, and Future Directions. Breast Cancer (Auckl) 7, 7-22.) and generate more positive effects than single-drug therapy. In other words, mTOR inhibitor rapamycin and ACSL4 inhibitor rosiglitazone can act in combination to inhibit tumor cell growth.

Example 2

Inhibition of Cell Proliferation Through the Combination of Sub-Effective Doses of Rosiglitazone and 4-Hydroxytamoxifen (4-OHTAM)

Figure 6:
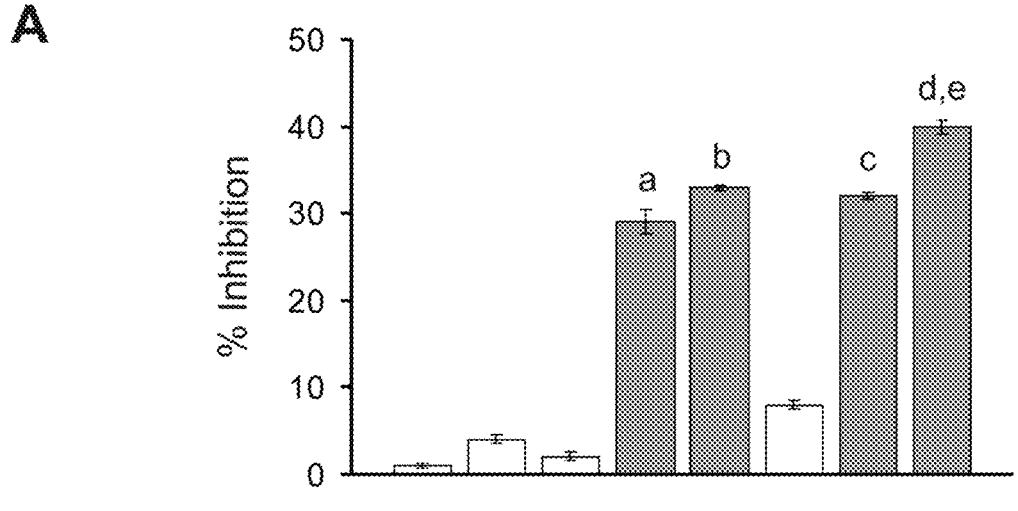
FIG. 6 shows the inhibition of cell proliferation through the combination of sub-maximal doses of ACSL4 and ER inhibitors. (A) MCF-7 Tet-Off/ACSL4 cells were plated and incubated with rosiglitazone (10 or 25 μM) and/or 4-hydroxytamoxifen (4-OHTAM, 2.5 or 5 μM) for 96 h. Subsequently, cell proliferation was measured by the bromo-deoxyuridine (BrdU) incorporation assay. Data is presented as percent inhibition of cell proliferation compared to control cells. White bars indicate a single inhibitor treatment while grey bars indicate a combined inhibitor treatment.
Figure 6:
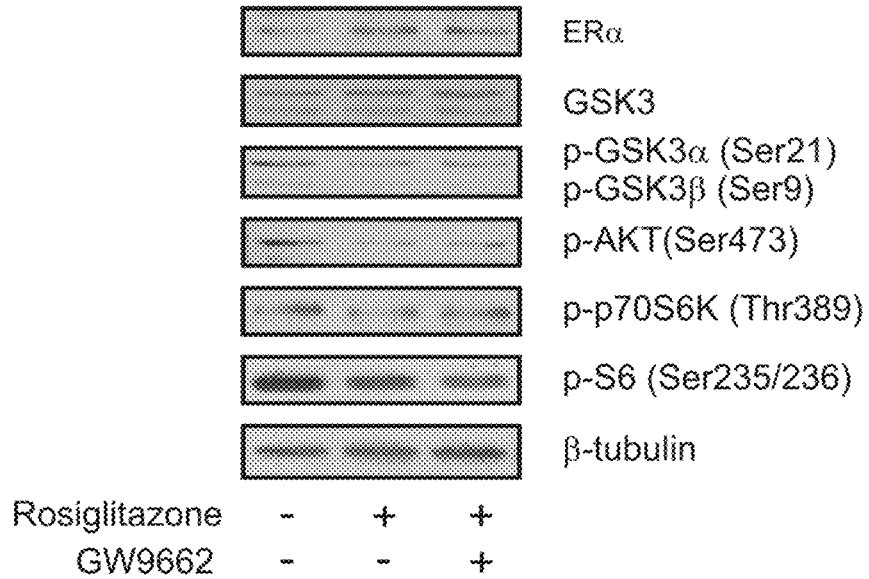

We have shown that knocking down ACSL4 expression in the aggressive triple negative breast cancer cell line MDA-MB-231 induces ERα expression (FIG. 6B). As expected, and in agreement with previous results (Orlando U. D. et al., 2012), ACSL4 overexpression decreases the level of ER (see FIG. 2), while targeting ACSL4 in cells and tumors reverses ER expression loss (Orlando U. D. et al., 2012). According to the present inventors' interpretation of these data, the inhibition of ACSL4 might force the tumor to restore the estrogen-signaling pathway for continuous growth and hormonal sensitivity, which is why the blockade of both the ACSL4 and estrogen pathways together might leave the tumor with extremely few options.

By means of the MCF-7 Tet-Off/ACSL4 model system, which involves a reduction in ER levels, a pharmacological approach to inhibit cell proliferation through a combination of 4-OHTAM and submaximal doses of rosiglitazone was used, which allows a significant effect of the two inhibitors. As shown in FIG. 6A, treatment with the inhibitors alone did not produce a significant inhibition in cell proliferation. However, the combination of the two inhibitors was much more efficient in inhibiting cell proliferation than 4-OHTAM or rosiglitazone individually, showing a remarkable synergistic effect. These results open up the possibility for inhibitor combinations which might prevent the loss of hormonal response in tumors that begin to overexpress ACSL4 and begin to reduce the levels of ER.

Following the same procedure as that described in Example 1 above, the cells were switched to 10% FBS-supplemented D-MEM medium and incubated with rosiglitazone (10 or 25 μM) and/or 4-hydroxytamoxifen (4-OHTAM, 2.5 or 5.0 μM). Both rosiglitazone and 4-hydroxytamoxifen were tested alone at each of the concentrations used, and in all the possible combinations with each other (see FIG. 6A).

|  | % inhibition of cell proliferation |
| --- | --- |
| 4-OHT 2.5 μM | 0.802 |
| 4-OHT 5 μM | 3.464 |
| Rosiglitazone 10 μM | 1.875 |
| Rosiglitazone 25 μM | 7.969 |
| 4-OHT 2.5 μM + Rosiglitazone 10 μM | 27.631 |
| 4-OHT 2.5 μM + Rosiglitazone 25 μM | 31.659 |
| 4-OHT 5 μM + Rosiglitazone 10 μM | 32.702 |
| 4-OHT 5 μM + Rosiglitazone 25 μM | 39.213 |

On the basis of these results, submaximal doses of rosiglitazone in combination with ER inhibitors, produce a significant inhibition of cell proliferation, thus preventing the side effects of supramaximal doses.

The present experimental assay demonstrates a synergistic effect on cell growth inhibition by the combination of rosiglitazone and tamoxifen, an estrogen receptor a (ERα) inhibitor.

Levels of ERα, p-S6, p-GSK3αβ, p-AKT (Ser473) and p-p70S6K were monitored to confirm that rosiglitazone treatment indeed increased ERα expression and decreased the mTOR signal as expected (FIG. 6B). These results are in agreement with previous results showing that mTOR inhibition by rapamycin reverses acquired endocrine therapy resistance of breast cancer cell and cell proliferation (Ghayad S E, Bieche I, Vendrell J A, Keime C, Lidereau R, Dumontet C and Cohen P A. mTOR inhibition reverses acquired endocrine therapy resistance of breast cancer cells at the cell proliferation and gene-expression levels. Cancer Sci. 2008; 99(10):1992-2003).

Since, as described above, the triple negative MDA-MB-231 breast cancer cells are sensitive to rosiglitazone, we also studied whether the inhibition of ACSL4 activity could reverse ER therapy resistance in cells that do not express ER. FIG. 7 shows the effect of a combination of rosiglitazone and 4-OHTAM on cell proliferation. The combination of the two inhibitors was much more efficient in inhibiting cell proliferation than 4-OHTAM or rosiglitazone individually. FIG. 7 inset shows again that rosiglitazone treatment indeed increased ERα expression, as shown in FIG. 6B. Again, these results suggest promising inhibitor combinations which might prevent the loss of hormonal response in triple negative tumors overexpressing ACSL4.

Example 3

In Vivo Therapy of Solid Tumors in Mice

On the basis of the above in vitro results and the demonstration that modulating ACSL4 inhibition results in the upregulation of ER with a consequent change in cell phenotype and the sensitivity of tamoxifen, the logical next step was to analyze the effect of ACSL4 inhibitor and tamoxifen on tumor growth in vivo.

The MDA-MB-231 cell line is known to form tumors with a triple negative signature that do not respond to hormone treatment; therefore, the MDA-MB-231 xenograft model was a very good challenge to demonstrate that ACSL4 inhibitor and ER inhibitor are working in a concerted manner and demonstrate a synergistic effect of the inhibitors as a potential therapeutic protocol.

The experimental design followed a well-established female nude mouse model, i.e., a nude mouse xenograft model. For this, MDA-MB-231 cells (5×106 cells) mixed with Matrigel Matrix (BD Biosciences) were injected into the right flank of female Foxn1 nu/nu Balb/c athymic nude mice, aged 6-8 weeks, and allowed to form tumors.

Tumors were measured with callipers every other day (length and width) and the mice were weighed. Mice were provided with free access to food, water and bedding at all time and were housed with a 12 h light/dark cycle in filter top cages containing a maximum of six mice per cage. Tumor volumes ($mm^3$) were calculated by the formula: $\pi/6 \times width^2$ ($mm^2$)$\times$length (mm) and the experiment was terminated as previously described in accordance with institutionally approved guidelines, (Orlando et al., 2012 supra).

For MDA-MB-231 tumor xenografts, four days after cell injection the tumor-bearing mice were randomized into the following four groups (five animals per group) and received intraperitoneal (ip) injections and oral administration of the respective drugs for 25 consecutive days.

The dose of the ACSL4 inhibitor used was calculated taking into account the minimal dose required for each individual inhibitor to produce a significant effect in the xenograft MDA-MB-231 model as previously described (Orlando et al., 2012 supra). Unitary doses were: rosiglitazone (0.6 mg/day) and tamoxifen (0.50 mg/day). In all cases, drugs were administered once a day by ip injection for rosiglitazone and tamoxifen was given through oral gavage during 25 days.

Group 1 (MDA-MB-231 cell xenografts treated with vehicle);
Group 2 (MDA-MB-231 cell xenografts treated with tamoxifen);
Group 3 (MDA-MB-231 cell xenografts treated with rosiglitazone); and
Group 4 (MDA-MB-231 cell xenografts treated with a combination of the two drugs at the same doses used for the individual injections).

Animals were maintained in pathogen-free conditions and procedures were performed in accordance with recommendations for the proper use and care of laboratory animals. Tumors were measured as described above. Individual animal weights were recorded before and after treatment.

Although the MDA-MB-231 xenograft growth rate varies among studies reported in the literature, our tumor xenografts were in the range of those previously reported (Orlando et al., 2012 supra). The average animal body weight was 23.5 g at the beginning of the treatment and no significant differences in body weight were observed between the different treatment groups at the end of the experiment. The amount of food intake in the control compared to the treated groups was not significantly different throughout the experiment. However, there was a significant inhibition in average tumor volume and growth rate in animals subjected to combination therapy compared to those that received single drug-based treatments or drug vehicle after injection of MDA-MB-231 cells (FIGS. 8A and 8B, respectively). The tumors from mice treated with drug combination were clearly smaller than those from either the control group or single drug treatment groups, thus showing the synergistic effect of the combination of inhibitors.

---

---

The invention claimed is:

1. A pharmaceutical composition for inhibiting tumor growth of an ACSL4-expressing tumor comprising a combination of: i) a first component which is an ACSL4 inhibitor which is rosiglitazone; and ii) a second component consisting of an ER inhibitor the ER inhibitor being selected from the group consisting of tamoxifen, bazedoxifene, lasofoxifene, ormeloxifene, raloxifene, clomifene, 4-OH-tamoxifen, toremifene, afimoxifene, endoxifen, idoxifen, droloxifen, N-demethyl-droloxifen, cis-tamoxifen, desethyltamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen and 4-hydroxy-N-demethyl-tamoxifen.

2. A pharmaceutical composition according to claim 1, wherein the first component is rosiglitazone and the second component is tamoxifen.

3. A method for inhibiting tumor growth of an ACSL4-expressing tumor, the method comprising administering to a subject in need thereof a combination of: i) a first component which is an ACSL4 inhibitor which is rosiglitazone; and ii)

a second component selected from an mTOR inhibitor and an ER inhibitor wherein the mTOR inhibitor is selected from the group consisting of rapamycin, temsirolimus, everolimus, tacrolimus, deforolimus, pimecrolimus, olcorolimus, zotarolimus and umirolimus, and the ER inhibitor is selected from tamoxifen, bazedoxifene, lasofoxifene, ormeloxifene, raloxifene, clomifene, 4-OH-tamoxifen, toremifene, afimoxifen, endoxifen, idoxifen, droloxifen, N-demethyl-droloxifen, cis-tamoxifen, desethyl-tamoxifen, N-desmethyl-tamoxifen, tamoxifen citrate, dihydro-tamoxifen, iodo-tamoxifen, 4-chlorotamoxifen, 4-methyl-tamoxifen, 4-fluoro-tamoxifen, 2-methyl-4-hydroxy-tamoxifen, deamino-hydroxy-tamoxifen, 4-hydroxy-deamino-hydroxy-tamoxifen and 4-hydroxy-N-demethyl-tamoxifen.

4. The method according to claim 3, wherein the first component is rosiglitazone and the second component is rapamycin.

5. The method according to claim 3, wherein the first component is rosiglitazone and the second component is tamoxifen.

6. The method according to claim 3, wherein the tumor is selected from the group consisting of colon carcinoma, hepatocellular carcinoma, and Triple Negative Breast Cancer (TNBC).

7. The method according to claim 3, wherein the tumor is triple negative breast cancer.

\* \* \* \* \*

SEQUENCE LISTING

<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: ACSL4 shRNA. Synthetic sequence designed to knock down ACSL4 expression.

<400> SEQUENCE: 1
aagattattc tgtggatga                                              19